(12) United States Patent
Ro et al.

(10) Patent No.: US 9,818,956 B2
(45) Date of Patent: *Nov. 14, 2017

(54) COMPOUND FOR ORGANIC PHOTOELECTRIC DEVICE AND ORGANIC PHOTOELECTRIC DEVICE, IMAGE SENSOR, AND ELECTRONIC DEVICE INCLUDING THE SAME

(71) Applicant: Samsung Electronics Co., Ltd., Suwon-si, Gyeonggi-do (KR)

(72) Inventors: Takkyun Ro, Hwaseong-si (KR); Seon-Jeong Lim, Yongin-si (KR); Kyung Bae Park, Hwaseong-si (KR); Sung Young Yun, Suwon-si (KR); Gae Hwang Lee, Seongnam-si (KR); Dong-Seok Leem, Hwaseong-si (KR); Yong Wan Jin, Seoul (KR); Yagi Tadao, Hwaseong-si (KR); Moon Gyu Han, Suwon-si (KR); Chuljoon Heo, Busan (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/931,413

(22) Filed: Nov. 3, 2015

(65) Prior Publication Data

US 2016/0126470 A1    May 5, 2016

(30) Foreign Application Priority Data

Nov. 4, 2014 (KR) .................... 10-2014-0152451

(51) Int. Cl.
*H01L 51/00* (2006.01)
*C09B 47/00* (2006.01)
*C09B 57/00* (2006.01)
*C07D 333/36* (2006.01)
*H01L 51/42* (2006.01)
*H01L 51/44* (2006.01)
*H01L 27/30* (2006.01)

(52) U.S. Cl.
CPC ........ *H01L 51/0061* (2013.01); *C07D 333/36* (2013.01); *C09B 47/00* (2013.01); *C09B 57/008* (2013.01); *H01L 27/307* (2013.01); *H01L 51/006* (2013.01); *H01L 51/008* (2013.01); *H01L 51/0046* (2013.01); *H01L 51/0053* (2013.01); *H01L 51/0067* (2013.01); *H01L 51/0068* (2013.01); *H01L 51/0074* (2013.01); *H01L 51/0058* (2013.01); *H01L 51/4253* (2013.01); *H01L 51/4293* (2013.01); *H01L 51/447* (2013.01); *H01L 2251/308* (2013.01)

(58) Field of Classification Search
CPC ............. H01L 51/0061; H01L 51/0053; H01L 51/0067; H01L 51/006; H01L 51/0046; H01L 51/0068; H01L 51/008; H01L 27/307; H01L 51/0074; H01L 2251/308; H01L 51/4253; H01L 51/447; H01L 51/4293; H01L 51/0058; C07D 333/36
See application file for complete search history.

(56) References Cited

U.S. PATENT DOCUMENTS

| | | | |
|---|---|---|---|
| 5,395,556 | A | 3/1995 | Drost et al. |
| 5,514,799 | A | 5/1996 | Varanasi et al. |
| 5,688,906 | A | 11/1997 | Jen et al. |
| 5,718,845 | A | 2/1998 | Drost et al. |
| 8,525,577 | B2 | 9/2013 | Yofu et al. |
| 9,070,887 | B2 | 6/2015 | Yofu et al. |
| 2011/0074491 | A1 | 3/2011 | Yofu et al. |
| 2013/0299799 | A1 | 11/2013 | Yofu et al. |

FOREIGN PATENT DOCUMENTS

| | | |
|---|---|---|
| EP | 0529162 A2 | 3/1993 |
| EP | 2317582 A1 | 5/2011 |
| JP | H05117542 A | 5/1993 |
| JP | H07173116 A | 7/1995 |
| KR | 2011-0035941 A | 4/2011 |

OTHER PUBLICATIONS

Bamfield, P., Chromic phenomena: technological applications of colour chemistry. Royal Society of Chemistry, 2010, p. 1-374.*
Claessens, et al. "Subphthalocyanines, Subporphyrazines, and Subporphyrins: Singular Nonplanar Aromatic Systems," Chemical Reviews, vol. 114, No. 4, pp. 2192-2277, (2014).
Extended European Search Report dated Mar. 10, 2016 issued in corresponding European Patent Application No. 15192821.5.
"Utilization of carboxylated 1, 3-indandione as an electron acceptor in dye-sensitized solar cells" Bull. Chem. Soc. Jap. vol. 85, pp. 1329-1331 (2012).

* cited by examiner

*Primary Examiner* — Matt Mauro
(74) *Attorney, Agent, or Firm* — Harness, Dickey & Pierce, P.L.C.

(57) ABSTRACT

A compound for an organic photoelectric device is represented by Chemical Formula 1. An organic photoelectric device includes a first electrode and a second electrode facing each other and an active layer between the first electrode and the second electrode, the active layer including the compound represented by Chemical Formula 1.

24 Claims, 19 Drawing Sheets

COMPOUND FOR ORGANIC PHOTOELECTRIC DEVICE AND ORGANIC PHOTOELECTRIC DEVICE, IMAGE SENSOR, AND ELECTRONIC DEVICE INCLUDING THE SAME

CROSS-REFERENCE TO RELATED APPLICATION

This application claims priority to and the benefit of Korean Patent Application No. 10-2014-0152451 filed in the Korean Intellectual Property Office on Nov. 4, 2014, the entire contents of which are incorporated herein by reference.

BACKGROUND

1. Field

Example embodiments provide a compound for an organic photoelectric device and an organic photoelectric device, an image sensor, and an electronic device including the same.

2. Description of the Related Art

A photoelectric device converts light into an electrical signal using photoelectric effects, and may include a photodiode and/or a phototransistor. The photoelectric device may be applied to an image sensor, a solar cell and/or an organic light emitting diode.

An image sensor including a photodiode requires relatively high resolution and thus a relatively small pixel. At present, a silicon photodiode is widely used, but may have a problem of deteriorated sensitivity since the silicon photodiode has a relatively small absorption area due to relatively small pixels. Accordingly, an organic material that is capable of replacing silicon has been researched.

The organic material has a relatively high extinction coefficient and selectively absorbs light in a particular wavelength region depending on a molecular structure, and thus may simultaneously replace a photodiode and a color filter and resultantly improve sensitivity and contribute to relatively high integration.

SUMMARY

Example embodiments provide a compound for an organic photoelectric device being capable of selectively absorbing light in a green wavelength region.

Example embodiments also provide an organic photoelectric device being capable of selectively absorbing light in a green wavelength region and improving efficiency.

Example embodiments also provide an image sensor and an electronic device including the compound for an organic photoelectric device.

According to example embodiments, a compound for an organic photoelectric device is represented by Chemical Formula 1.

[Chemical Formula 1]

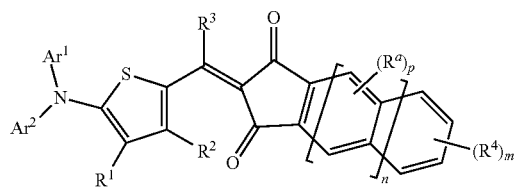

In Chemical Formula 1, each of $Ar^1$ and $Ar^2$ are independently one of a phenyl group and a naphthyl group, provided at least one of $Ar^1$ and $Ar^2$ is a naphthyl group, each of $R^1$ to $R^4$ are independently one of hydrogen, a $C_1$ to $C_6$ alkyl group, a $C_1$ to $C_6$ haloalkyl group, a halogen, and CN, $R^a$ is one of hydrogen, a $C_1$ to $C_6$ alkyl group, a $C_1$ to $C_6$ haloalkyl group, a halogen, and CN, p is an integer of 1 or 2, n is 0 or 1, m is an integer ranging from 1 to 4, and the compound has 7 aromatic rings.

The compound may be represented by Chemical Formula 2.

[Chemical Formula 2]

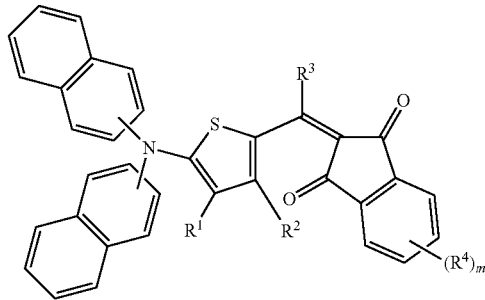

In Chemical Formula 2, each of $R^1$ to $R^4$ are independently one of hydrogen, a $C_1$ to $C_6$ alkyl group, a $C_1$ to $C_6$ haloalkyl group, a halogen, and CN, and m is an integer ranging from 1 to 4.

The compound may be represented by Chemical Formula 3.

[Chemical Formula 3]

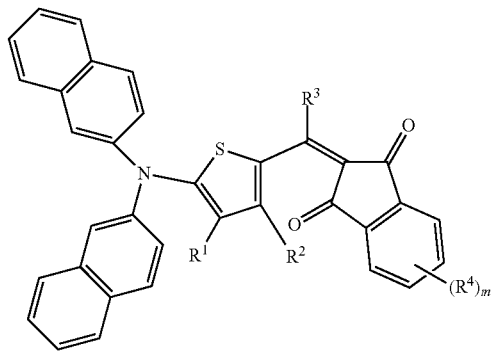

In Chemical Formula 3, each of $R^1$ to $R^4$ are independently one of hydrogen, a $C_1$ to $C_6$ alkyl group, a $C_1$ to $C_6$ haloalkyl group, a halogen, and CN, and m is an integer ranging from 1 to 4.

The compound may be represented by Chemical Formula 4.

[Chemical Formula 4]

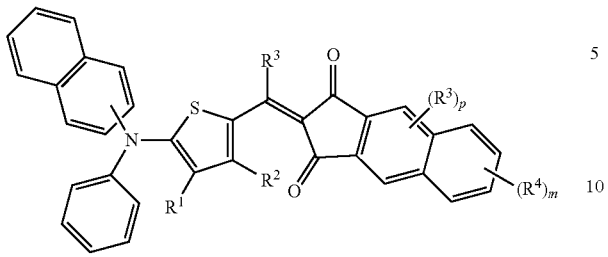

In Chemical Formula 4,
each of $R^1$ to $R^4$ are independently one of hydrogen, a $C_1$ to $C_6$ alkyl group, a $C_1$ to $C_6$ haloalkyl group, a halogen, and CN, $R^a$ is one of hydrogen, a $C_1$ to $C_6$ alkyl group, a $C_1$ to $C_6$ haloalkyl group, a halogen, and CN, p is an integer of 1 or 2, and m is an integer ranging from 1 to 4.

The compound may be represented by Chemical Formula 5.

[Chemical Formula 5]

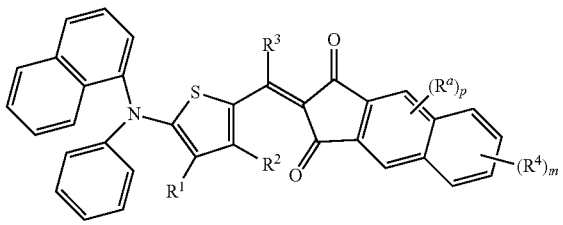

In Chemical Formula 5,
each of $R^1$ to $R^4$ are independently one of hydrogen, a $C_1$ to $C_6$ alkyl group, a $C_1$ to $C_6$ haloalkyl group, a halogen, and CN, $R^a$ is one of hydrogen, a $C_1$ to $C_6$ alkyl group, a $C_1$ to $C_6$ haloalkyl group, a halogen, and CN, p is an integer of 1 or 2, and m is an integer ranging from 1 to 4.

The compound may show a light absorption curve having a full width at half maximum (FWHM) of about 50 nm to about 100 nm in a thin film state.

The compound may have a maximum absorption wavelength ($\lambda_{max}$) of about 530 nm to about 570 nm in a thin film state.

The compound may be a p-type semiconductor compound.

According to example embodiments, a compound for an organic photoelectric device is represented by Chemical Formula 1, the compound has a maximum absorption wavelength ($\lambda_{max}$) of about 530 nm to about 570 nm in a thin film state.

According to example embodiments, an organic photoelectric device includes a first electrode and a second electrode facing each other, and an active layer between the first electrode and the second electrode, the active layer including the compound represented by Chemical Formula 1.

The active layer may further include an n-type semiconductor compound.

The n-type semiconductor compound may be one of sub-phthalocyanine, fullerene or a fullerene derivative, thiophene or a thiophene derivative, and a combination thereof.

The active layer may include an intrinsic layer including the compound represented by Chemical Formula 1.

The active layer may further include at least one of a p-type layer on one side of the intrinsic layer and an n-type layer on the other side of the intrinsic layer.

The active layer may further include a second p-type semiconductor compound configured to selectively absorb green light. The p-type semiconductor compound may be represented by Chemical Formula 9.

[Chemical Formula 9]

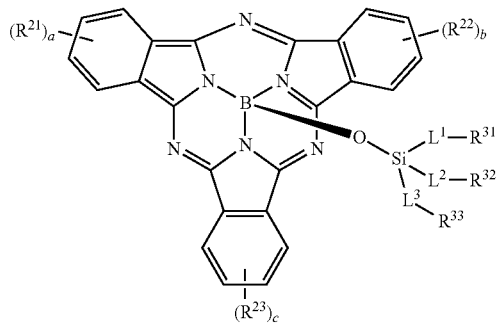

In Chemical Formula 9,
each of $R^{21}$ to $R^{23}$ are independently one of hydrogen, a substituted or unsubstituted $C_1$ to $C_{30}$ aliphatic hydrocarbon group, a substituted or unsubstituted $C_6$ to $C_{30}$ aromatic hydrocarbon group, a substituted or unsubstituted $C_1$ to $C_{30}$ aliphatic heterocyclic group, a substituted or unsubstituted $C_2$ to $C_{30}$ aromatic heterocyclic group, a substituted or unsubstituted $C_1$ to $C_{30}$ alkoxy group, a substituted or unsubstituted $C_6$ to $C_{30}$ aryloxy group, a thiol group, a substituted or unsubstituted $C_1$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group, and a combination thereof, $R^{21}$ to $R^{23}$ are independently present or are fused to each other to provide a ring, each of $L^1$ to $L^3$ are independently one of a single bond, a substituted or unsubstituted $C_1$ to $C_{30}$ alkylene group, a substituted or unsubstituted $C_6$ to $C_{30}$ arylene group, a divalent substituted or unsubstituted $C_3$ to $C_{30}$ heterocyclic group, and a combination thereof, and each of $R^{31}$ to $R^{33}$ are independently one of a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group, a substituted or unsubstituted silyl group, and a combination thereof.

According to example embodiments, an image sensor includes the organic photoelectric device of example embodiments.

The image sensor may include a semiconductor substrate integrated with a plurality of first photo-sensing devices configured to sense light in a blue wavelength region and a plurality of second photo-sensing devices configured to sense light in a red wavelength region, wherein the organic photoelectric device is on the semiconductor substrate and configured to selectively absorb light in a green wavelength region.

The image sensor may further include a color filter layer between the semiconductor substrate and the organic photoelectric device, the color filter layer including a blue filter configured to selectively absorb light in a blue wavelength region and a red filter configured to selectively absorb light in a red wavelength region.

The image sensor may further include a semiconductor substrate integrated with at least one photo-sensing device, wherein the organic photoelectric device is on the semiconductor substrate.

The at least one photo-sensing device may include a first photo-sensing device configured to sense light in a blue wavelength region and a second photo-sensing device configured to sense light in a red wavelength region, and the first photo-sensing device and the second photo-sensing device may be stacked in a vertical direction on the semiconductor substrate.

The organic photoelectric device may be a green photoelectric device, and the green photoelectric device, a blue photoelectric device configured to selectively absorb light in a blue wavelength region, and a red photoelectric device configured to selectively absorb light in a red wavelength region may be stacked.

The compound included in the active layer may be a p-type semiconductor compound, the active layer may further include an n-type semiconductor compound, and the p-type semiconductor compound and the n-type semiconductor compound may form a pn junction.

According to example embodiments, an electronic device includes the compound of example embodiments.

DETAILED DESCRIPTION

Figure 1:
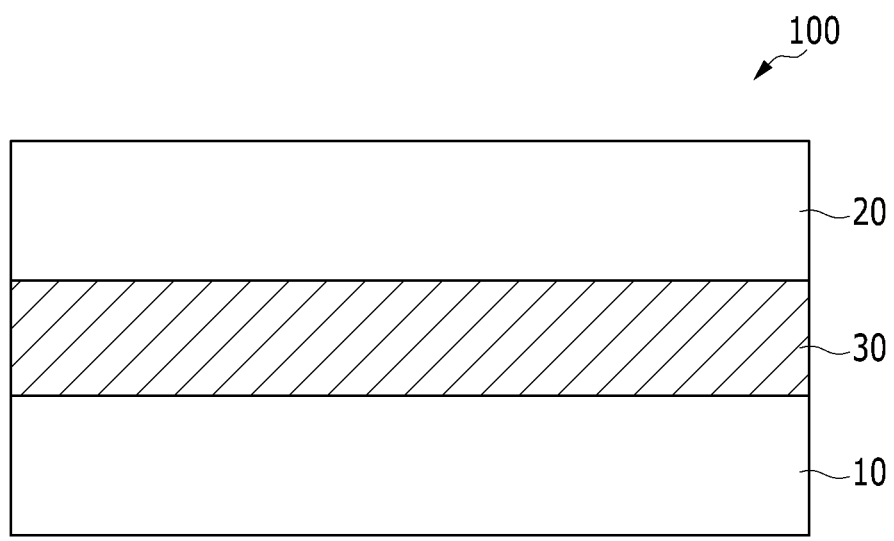
FIG. 1 is a cross-sectional view showing an organic photoelectric device according to example embodiments.

Example embodiments of the present inventive concepts will hereinafter be described in detail, and may be more easily performed by those who have common knowledge in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when specific definition is not otherwise provided, the term "hetero" refers to one including 1 to 3 heteroatoms selected from N, O, S, and P.

As used herein, when specific definition is not otherwise provided, the term "substituted" refers to a functional group substituted with a substituent selected from a halogen (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a $C_1$ to $C_{20}$ alkoxy group, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{20}$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen.

As used herein, when specific definition is not otherwise provided, the term "aromatic ring" refers to a substituted or unsubstituted 5-membered to 8-membered ring having a conjugation structure, for example a substituted or unsubstituted 5-membered or 6-membered ring having a conjugation structure. The ring may have 1 to 3 heteroatoms selected from N, O, S, and P.

As used herein, when specific definition is not otherwise provided, the term "cyano-containing group" refers to a $C_1$ to $C_{30}$ alkyl group, a $C_2$ to $C_{30}$ alkenyl group, or a $C_2$ to $C_{30}$ alkynyl group where at least one hydrogen is replaced by a cyano group.

As used herein, when specific definition is not otherwise provided, the term "halogen-containing group" refers to a $C_1$ to $C_{30}$ alkyl group, a $C_2$ to $C_{30}$ alkenyl group or a $C_2$ to $C_{30}$ alkynyl group where at least one hydrogen is replaced by a halide group (—F, —Cl, —Br, or —I).

Hereinafter, a compound for an organic photoelectric device according to example embodiments is described.

A compound for an organic photoelectric device according to example embodiments is represented by Chemical Formula 1.

[Chemical Formula 1]

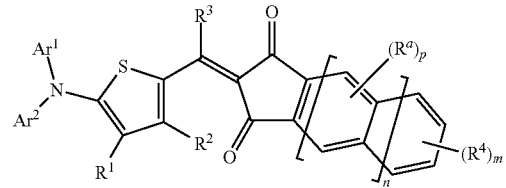

In Chemical Formula 1, each of $Ar^1$ and $Ar^2$ are independently one of a phenyl group and a naphthyl group, provided at least one of $Ar^1$ and $Ar^2$ is a naphthyl group, each of $R^1$ to $R^4$ are independently one of hydrogen, a $C_1$ to $C_6$ alkyl group, a $C_1$ to $C_6$ haloalkyl group, a halogen, and CN, $R^a$ is one of hydrogen, a $C_1$ to $C_6$ alkyl group, a $C_1$ to $C_6$ haloalkyl group, a halogen, and CN, p is an integer of 1 or 2, n is 0 or 1, m is an integer ranging from 1 to 4, for example, 1 to 3, and the compound has 7 aromatic rings.

In Chemical Formula 1, when m is greater than or equal to 2, each $R^4$ may be different.

In Chemical Formula 1, when n is 0, $Ar^1$ and $Ar^2$ may be each a naphthyl group. In example embodiments, the compound for an organic photoelectric device may be represented by Chemical Formula 2.

[Chemical Formula 2]

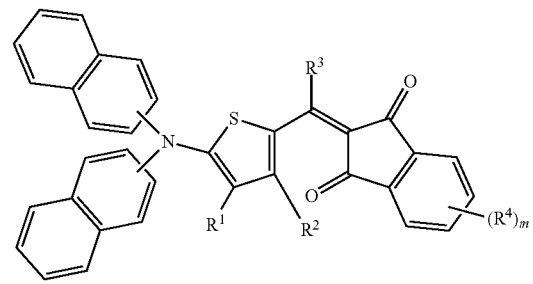

In Chemical Formula 2, each of $R^1$ to $R^4$ are independently one of hydrogen, a $C_1$ to $C_6$ alkyl group, a $C_1$ to $C_6$ haloalkyl group, a halogen, and CN, and m is an integer ranging from 1 to 4, for example, 1 to 3.

In Chemical Formula 1, when n is 0, $Ar^1$ and $Ar^2$ may be each a naphthyl group, and nitrogen (N) may be bonded at the 2 position of the naphthyl group. In example embodiments, the compound for an organic photoelectric device may be represented by Chemical Formula 3.

[Chemical Formula 3]

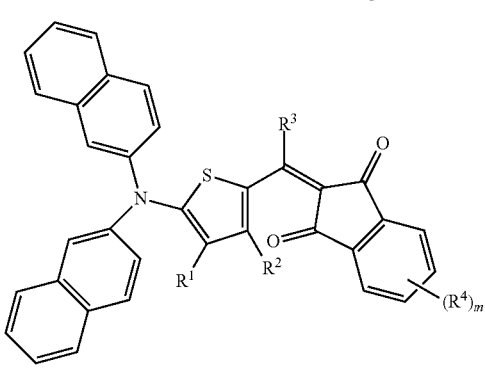

In Chemical Formula 3, each of $R^1$ to $R^4$ are independently one of hydrogen, a $C_1$ to $C_6$ alkyl group, a $C_1$ to $C_6$ haloalkyl group, a halogen, and CN, and m is an integer ranging from 1 to 4, for example, 1 to 3.

In Chemical Formulae 2 and 3, when m is greater than or equal to 2, each $R^4$ may be the same or different.

In Chemical Formula 1, when n is 1, one of $Ar^1$ and $Ar^2$ may be a naphthyl group and the other may be a phenyl group. In example embodiments, the compound for an organic photoelectric device may be represented by Chemical Formula 4.

[Chemical Formula 4]

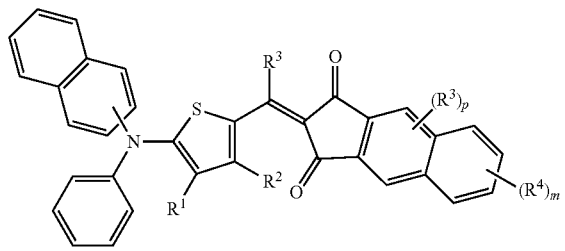

In Chemical Formula 4, each of $R^1$ to $R^4$ are independently one of hydrogen, a $C_1$ to $C_6$ alkyl group, a $C_1$ to $C_6$ haloalkyl group, a halogen, and CN, $R^a$ is one of hydrogen, a $C_1$ to $C_6$ alkyl group, a $C_1$ to $C_6$ haloalkyl group, a halogen, and CN, p is an integer of 1 or 2, and m is an integer ranging from 1 to 4, for example, 1 to 3.

In Chemical Formula 1, when n is 1, one of $Ar^1$ and $Ar^2$ may be a naphthyl group and the other may be a phenyl group, and nitrogen (N) may be bonded at the 1 position of the naphthyl group. In example embodiments, the compound for an organic photoelectric device may be represented by Chemical Formula 5.

[Chemical Formula 5]

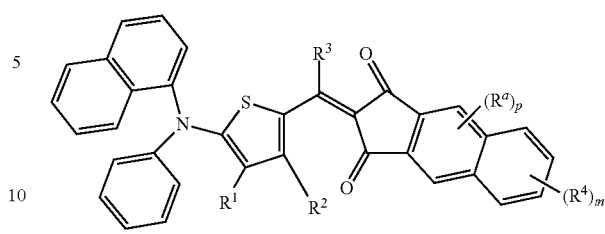

In Chemical Formula 5, each of $R^1$ to $R^4$ are independently one of hydrogen, a $C_1$ to $C_6$ alkyl group, a $C_1$ to $C_6$ haloalkyl group, a halogen, and CN, $R^a$ is one of hydrogen, a $C_1$ to $C_6$ alkyl group, a $C_1$ to $C_6$ haloalkyl group, a halogen, and CN, p is an integer of 1 or 2, and m is an integer ranging from 1 to 4, for example, 1 to 3.

In Chemical Formulae 4 and 5, when m is greater than or equal to 2, each $R^4$ may be the same or different, and when p is 2, each $R^a$ may be the same or different.

The halogen refers to F, Cl, Br, or I, and the haloalkyl group refers to an alkyl group where at least one hydrogen is substituted with F, Cl, Br, or I. Specific examples of the haloalkyl group may be a fluoroalkyl group, for example, a perfluoroalkyl group.

The compound for an organic photoelectric device includes an electron donor moiety and an electron acceptor moiety inside one molecule, and thus has a bipolar characteristic. The compound for an organic photoelectric device overall has seven aromatic rings forming a conjugation structure. When there are less than seven aromatic rings, a maximum absorption wavelength is shifted toward blue, and thus selective absorption of green is deteriorated. In addition, when there are more than seven aromatic rings, the maximum absorption wavelength is shifted toward red, and thus selective absorption of green is also deteriorated.

Furthermore, the compound for an organic photoelectric device has a structure in which at least one substituent bonded to nitrogen (N) in Chemical Formula 1 for $Ar^1$ and $Ar^2$ is a naphthyl group. When at least one substituent for $Ar^1$ and $Ar^2$ is a naphthyl group, an intermolecular interaction in a film state is decreased, and thus aggregation among molecules is prevented or reduced. The aggregation among molecules moves a wavelength in a light absorption curve toward red and brings about a broad absorption peak. Accordingly, the compound for an organic photoelectric device has a naphthyl group for at least one of $Ar^1$ and $Ar^2$, and thus may increase selectivity about a green wavelength region. On the contrary, when the $Ar^1$ and $Ar^2$ are all alkyl groups or phenyl groups, a compound has a flat structure and thus too wide a full width at half maximum (FWHM) in a light absorption curve. In addition, when one of the $Ar^1$ and $Ar^2$ is a phenyl group and the other is a biphenyl group, that is, there is no naphthyl group, a conjugation structure between the phenyl group and one phenyl group of the biphenyl group is broken and may not provide a favorable conjugation length. Furthermore, when the $Ar^1$ and $Ar^2$ are fused with each other and form an N-containing ring, a compound has a flat structure and thus too wide a full width at half maximum (FWHM) in a light absorption curve. When the aromatic groups of the $Ar^1$ and $Ar^2$ are heteroaryl groups including sulfur (S), a wavelength in a light absorption curve may be shifted toward red, and when a heteroatom of nitrogen (N) or oxygen (O) is included therein, stability of a compound may be deteriorated.

The compound for an organic photoelectric device may show a light absorption curve having a full width at half maximum (FWHM) of about 50 nm to about 100 nm, and specifically about 50 nm to about 90 nm in a thin film state. Herein, the FWHM is a width of a wavelength corresponding to a half of a height of a maximum absorption point. As used herein, when specific definition is not otherwise provided, it may be defined by absorbance measured by UV-Vis spectroscopy. A smaller FWHM indicates selective absorption of light in a narrow wavelength region and high wavelength selectivity. The thin film may be a thin film deposited under a vacuum condition.

The compound for an organic photoelectric device is a compound selectively absorbing light in a green wavelength region, and may have a maximum absorption wavelength ($\lambda_{max}$) at about 530 nm to about 570 nm.

The compound for an organic photoelectric device may have a HOMO level about 5.2 to about 5.5 eV, and an energy bandgap of about 1.9 to about 2.3 eV. The compound for an organic photoelectric device having a HOMO level and an energy bandgap within the ranges may be used as a p-type semiconductor compound effectively absorbing light in a green wavelength region, and thus has high external quantum efficiency (EQE) and resultantly improves photoelectric conversion efficiency.

The compound for an organic photoelectric device may have a molecular weight of about 300 to about 1500, more specifically about 350 to about 1200, and even more specifically about 400 to about 900. When the compound has a molecular weight within the range, the crystallinity of the compound and thermal decomposition during formation of a thin film by deposition may be inhibited.

The compound for an organic photoelectric device may have a melting point of greater than or equal to about 200° C., for example, greater than or equal to about 250° C., and for example, greater than or equal to about 280° C. When the compound has a melting point within the range, a thin film may be stably deposited and an amount of a decomposed product is decreased, and thus an organic photoelectric device having improved photoelectric conversion performance is provided.

Hereinafter, an organic photoelectric device including the compound according to example embodiments is described with reference to drawings.

FIG. 1 is a cross-sectional view showing an organic photoelectric device according to example embodiments.

Referring to FIG. 1, an organic photoelectric device 100 according to example embodiments includes a first electrode 10 and a second electrode 20, and an active layer 30 interposed between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor (e.g., indium tin oxide (ITO) or indium zinc oxide (IZO)), or a metal thin layer of a thin monolayer or multilayer. When one of the first electrode 10 and the second electrode 20 is a non-light-transmitting electrode, the one of the first electrode 10 and the second electrode 20 may be made of, for example, an opaque conductor (e.g., aluminum (Al)).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound for an organic photoelectric device may act as a p-type semiconductor compound in the active layer 30.

The compound for an organic photoelectric device is a compound selectively absorbing light in a green wavelength region, and the active layer 30 including the compound may have a maximum absorption wavelength ($\lambda_{max}$) at about 530 nm to about 570 nm, which may selectively absorb light in a green wavelength region.

The active layer 30 may show a light absorption curve having a full width at half maximum (FWHM) of about 50 nm to about 100 nm, and specifically about 50 nm to about 90 nm in a thin film state. Accordingly, the active layer 30 has high selectivity for light in a green wavelength region.

The active layer 30 may further include an n-type semiconductor compound for forming a pn junction.

The n-type semiconductor compound may be one of sub-phthalocyanine, fullerene or a fullerene derivative, thiophene or a thiophene derivative, and a combination thereof. The fullerene may include fullerene C60, fullerene C70, fullerene C76, fullerene C78, fullerene C80, fullerene C82, fullerene C84, fullerene C90, fullerene C96, fullerene C240, fullerene C540, mixed fullerene, fullerene nanotube, and the like. The "fullerene derivatives" may refer to compounds of these fullerenes having a substituent attached thereto. The fullerene derivatives may include substituents such as alkyl groups, aryl groups, or heterocyclic groups. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxathin ring, a phenothiazine ring, or a phenazine ring.

The sub-phthalocyanine may be represented by Chemical Formula 6.

[Chemical Formula 6]

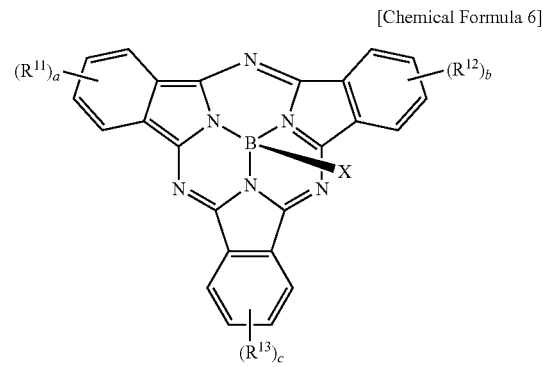

In Chemical Formula 6,
each of $R^{11}$ to $R^{13}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a halogen-containing group, and a combination thereof, a, b, and c are integers ranging from 1 to 3, and X is a halogen, for example, one of F and Cl.

The halogen refers to one of F, Cl, Br, and I, and the haloalkyl group refers to an alkyl group where at least one hydrogen is substituted with one of F, Cl, Br, and I.

The thiophene derivative may be, for example represented by Chemical Formula 7 or Chemical Formula 8, but is not limited thereto.

[Chemical Formula 7]

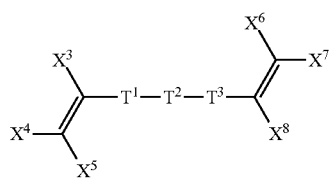

[Chemical Formula 8]

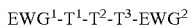

$EWG^1$-$T^1$-$T^2$-$T^3$-$EWG^2$

In Chemical Formulae 7 and 8, $T^1$, $T^2$, and $T^3$ are aromatic rings including substituted or unsubstituted thiophene moieties, each of $T^1$, $T^2$, and $T^3$ are independently present or are fused to each other, each of $X^3$ to $X^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a cyano group, and a combination thereof, and $EWG^1$ and $EWG^2$ are independently electron withdrawing groups.

For example, in Chemical Formula 7, at least one of $X^3$ to $X^8$ is an electron withdrawing group, for example a cyano group.

The active layer 30 may further include a second p-type semiconductor compound selectively absorbing green light. The p-type semiconductor compound may be a compound represented by Chemical Formula 9.

[Chemical Formula 9]

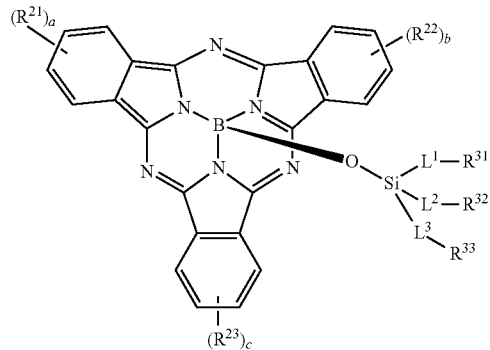

In Chemical Formula 9, each of $R^{21}$ to $R^{23}$ are independently one of hydrogen, a substituted or unsubstituted $C_1$ to $C_{30}$ aliphatic hydrocarbon group, a substituted or unsubstituted $C_6$ to $C_{30}$ aromatic hydrocarbon group, a substituted or unsubstituted $C_1$ to $C_{30}$ aliphatic heterocyclic group, a substituted or unsubstituted $C_2$ to $C_{30}$ aromatic heterocyclic group, a substituted or unsubstituted $C_1$ to $C_{30}$ alkoxy group, a substituted or unsubstituted $C_6$ to $C_{30}$ aryloxy group, a thiol group, a substituted or unsubstituted $C_1$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group (e.g., a substituted or unsubstituted $C_0$ to $C_{30}$ aminosulfonyl group, a substituted or unsubstituted $C_1$ to $C_{30}$ alkylsulfonyl group, or a substituted or unsubstituted $C_6$ to $C_{30}$ arylsulfonyl group), and a combination thereof, $R^{21}$ to $R^{23}$ are independently present or are fused to each other to provide a ring, each of $L^1$ to $L^3$ are independently one of a single bond, a substituted or unsubstituted $C_1$ to $C_{30}$ alkylene group, a substituted or unsubstituted $C_6$ to $C_{30}$ arylene group, a divalent substituted or unsubstituted $C_3$ to $C_{30}$ heterocyclic group, and a combination thereof, and each of $R^{31}$ to $R^{33}$ are independently one of a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group (e.g., a substituted or unsubstituted $C_1$ to $C_{30}$ alkylamine group or a substituted or unsubstituted $C_6$ to $C_{30}$ arylamine group), a substituted or unsubstituted silyl group, and a combination thereof.

The second p-type semiconductor compound selectively absorbing green light may be included in an amount of about 500 to about 1500 parts by weight based on 100 parts by weight of the compound of Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, and a p-type layer/n-type layer.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced and a pn junction may be effectively formed.

The p-type layer may include the compound of Chemical Formula 1, and the n-type layer may include the n-type semiconductor compound.

The active layer 30 may have a thickness of about 1 nm to about 500 nm, and specifically, about 5 nm to about 300 nm. When the active layer 30 has a thickness within the range, the active layer may effectively absorb light, effectively separate holes from electrons, and deliver them, thereby effectively improving photoelectric conversion efficiency. An optimal thickness of a thin film may be, for example, determined by an absorption coefficient of the active layer 30, and may be, for example, a thickness being capable of absorbing light of at least about 70% or more, for example about 80% or more, and for another example about 90%.

In the organic photoelectric device 100, when light enters from the first electrode 10 and/or second electrode 20, and when the active layer 30 absorbs light having a predetermined or given wavelength region, excitons may be produced from the inside. The excitons are separated into holes and electrons in the active layer 30, and the separated holes are transported to an anode that is one of the first electrode 10 and second electrode 20 and the separated electrons are transported to the cathode that is the other of and the first electrode 10 and second electrode 20 so as to flow a current in the organic photoelectric device.

Hereinafter, an organic photoelectric device according to example embodiments is described with reference to FIG. 2.

Figure 2:
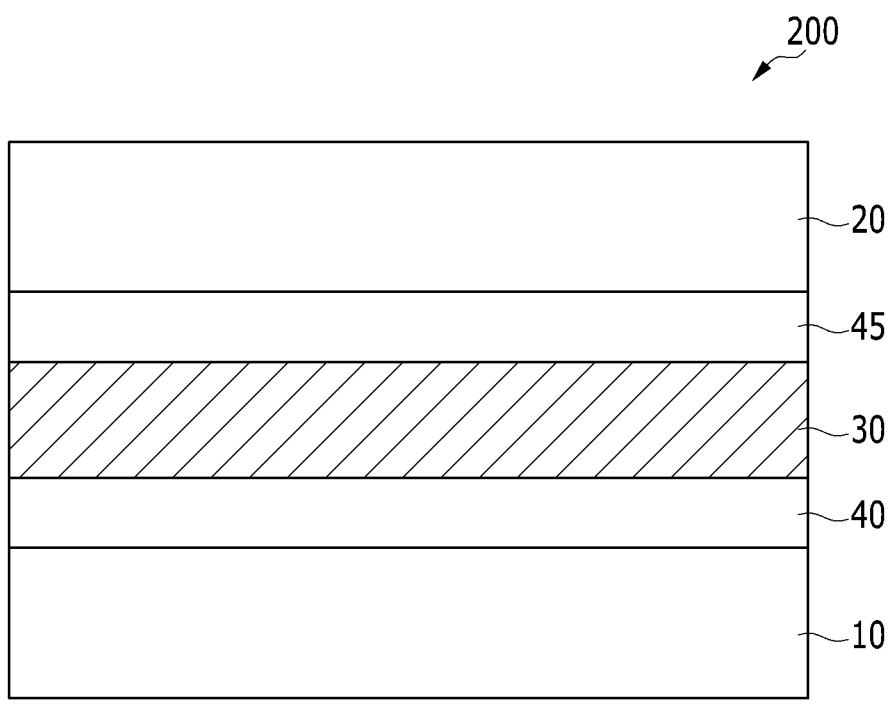
FIG. 2 is a cross-sectional view of an organic photoelectric device according to example embodiments.

FIG. 2 is a cross-sectional view showing an organic photoelectric device according to example embodiments.

Referring to FIG. 2, an organic photoelectric device 200 includes a first electrode 10 and a second electrode 20 facing each other, and an active layer 30 interposed between the first electrode 10 and the second electrode 20, like the example embodiment illustrated in FIG. 1.

However, the organic photoelectric device 200 according to the example embodiment illustrated in FIG. 2 further includes charge auxiliary layers 40 and 45 between the first electrode 10 and the active layer 30, and the second electrode 20 and the active layer 30, unlike the example embodiment illustrated in FIG. 1. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing or inhibiting electron transport, an electron injection layer (EIL) for facilitating electron injection, an electron transport layer (ETL) for facilitating electron transport, and a hole blocking layer (HBL) for preventing or inhibiting hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide (e.g., molybdenum oxide, tungsten oxide, and nickel oxide).

The hole transport layer (HTL) may include one selected from, for example, poly(3,4-ethylenedioxythiophene):poly(styrenesulfonate) (P EDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The organic photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
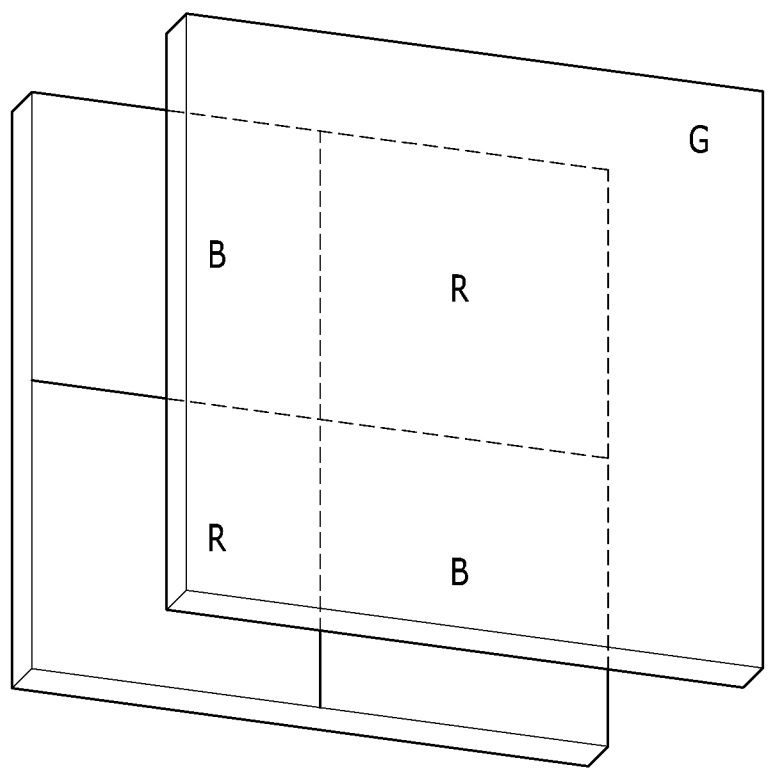
FIG. 3 is a schematic top plan view showing an organic CMOS image sensor according to example embodiments.
Figure 4:
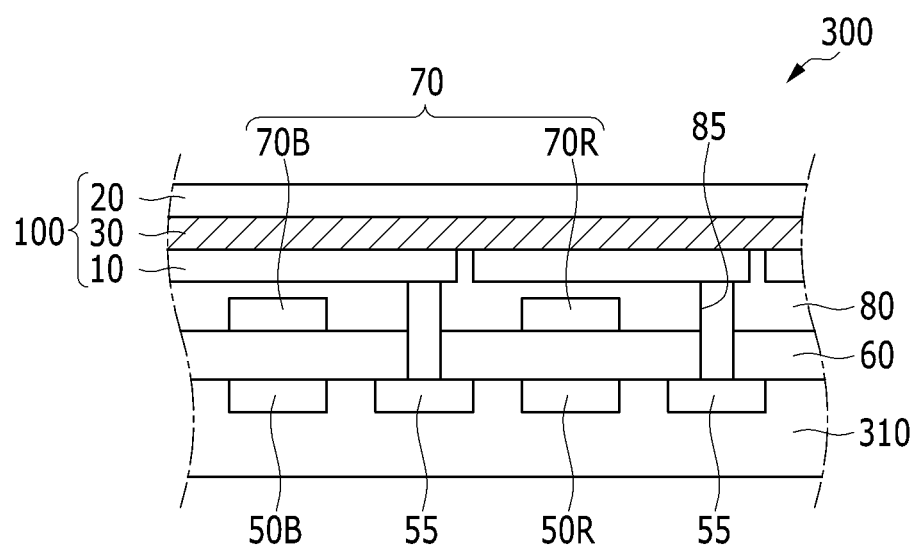
FIG. 4 is a cross-sectional view showing the organic CMOS image sensor of FIG. 3.

FIG. 3 is a schematic top plan view of an organic CMOS image sensor according to example embodiments, and FIG. 4 is a cross-sectional view of the organic CMOS image sensor of FIG. 3.

Referring to FIGS. 3 and 4, an organic CMOS image sensor 300 according to example embodiments includes a semiconductor substrate 310 integrated with photo-sensing devices 50B and 50R, a transmission transistor (not shown), a charge storage 55, a lower insulation layer 60, a color filter layer 70, an upper insulation layer 80, and an organic photoelectric device 100.

The semiconductor substrate 310 may be a silicon substrate, and is integrated with the photo-sensing devices 50B and 50R, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected with the organic photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material (e.g., a silicon oxide and/or a silicon nitride), or a low dielectric constant (low K) material (e.g., SiC, SiCOH, SiCO, and SiOF). The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and a red filter 70R filled in the red pixel. In example embodiments, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothes the surface. The upper insulation layer 80 and the lower insulation layer 60 may include a contact hole (not shown) exposing a pad, and a through-hole 85 exposing the charge storage 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the organic photoelectric devices selectively absorbing light in a green wavelength region are stacked and thereby a size of an image sensor may be decreased and a down-sized image sensor may be realized.

Figure 5:
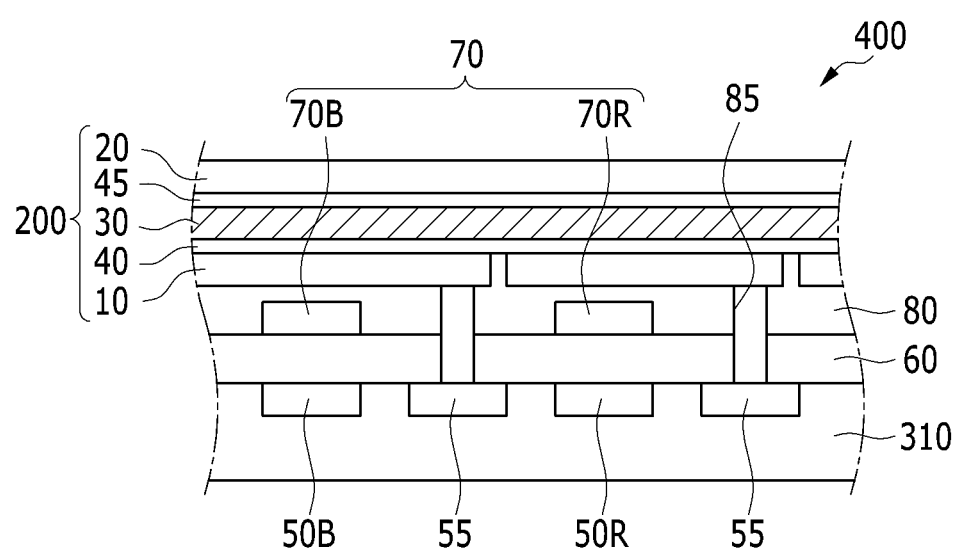
FIG. 5 is a schematic cross-sectional view showing an organic CMOS image sensor according to example embodiments.

In FIG. 4, the organic photoelectric device 100 of FIG. 1 is included, but it is not limited thereto, and thus the organic photoelectric device 200 of FIG. 2 may be applied in the same manner. FIG. 5 shows a structure of an image sensor having such a structure, and is a cross-sectional view of an organic CMOS image sensor 400 including the organic photoelectric device 200 in FIG. 2.

Figure 6:
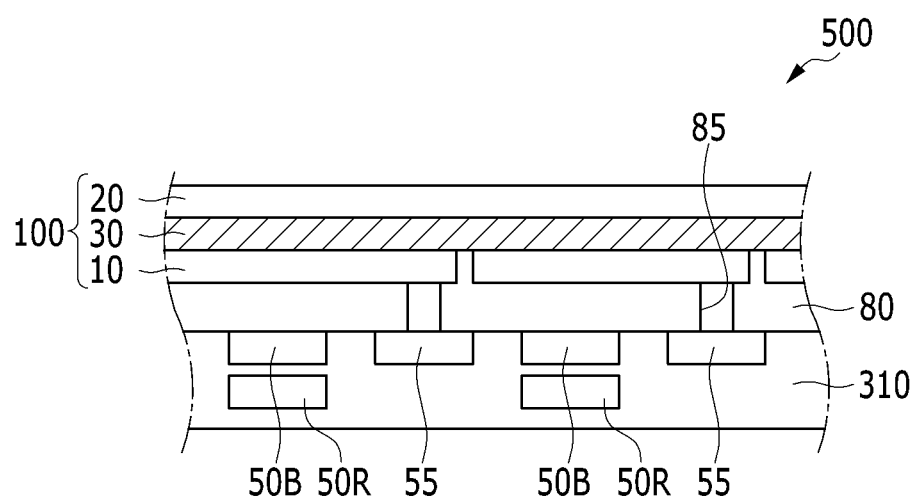
FIG. 6 is a cross-sectional view showing the organic CMOS image sensor according to example embodiments.

FIG. 6 is a cross-sectional view showing the organic CMOS image sensor according to example embodiments.

Referring to FIG. 6, the organic CMOS image sensor 500 includes a semiconductor substrate 310 integrated with photo-sensing devices 50B and 50R, a transmission transistor (not shown), a charge storage 55, an insulation layer 80, and an organic photoelectric device 100, like the example embodiment illustrated in FIG. 5.

However, the organic CMOS image sensor 500 according to the example embodiment illustrated in FIG. 6 includes the blue photo-sensing device 50B and the red photo-sensing device 50R that are stacked and does not include a color filter layer 70, unlike the example embodiment illustrated in FIG. 5. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the organic photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the organic photoelectric device 100 has improved green wavelength selectivity, and crosstalk caused by unnecessary absorption light in a wavelength region except green may be decreased while increasing sensitivity.

In FIG. 6, the organic photoelectric device 100 of FIG. 1 is included, but it is not limited thereto, and thus the organic photoelectric device 200 of FIG. 2 may be applied in the same manner.

Figure 7:
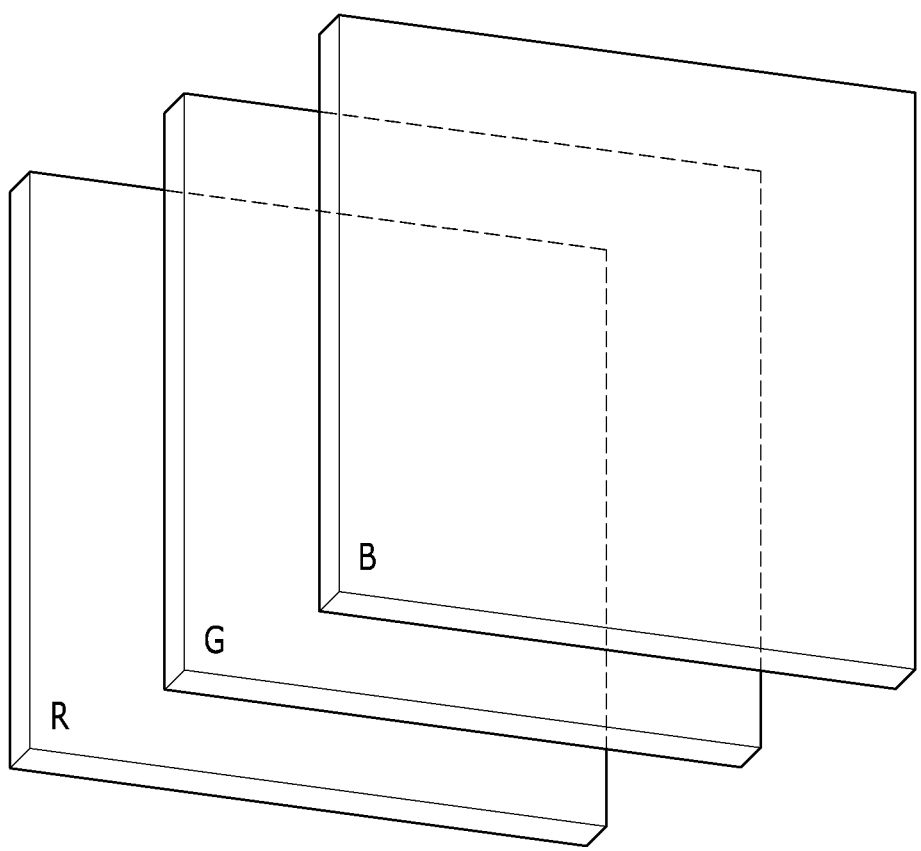
FIG. 7 is a schematic top plan view showing an organic CMOS image sensor according to example embodiments.

FIG. 7 is a schematic top plan view showing an organic CMOS image sensor according to example embodiments.

Referring to FIG. 7, the organic CMOS image sensor includes a green photoelectric device (G) selectively absorbing light in a green wavelength region, a blue photoelectric device (B) selectively absorbing light in a blue wavelength region, and a red photoelectric device selectively absorbing light in a red wavelength region that are stacked.

In the drawing, the red photoelectric device, the green photoelectric device, and the blue photoelectric device are sequentially stacked, but the stack order may be changed without limitation.

The green photoelectric device may be the above organic photoelectric device 100, the blue photoelectric device may include electrodes facing each other and an active layer interposed therebetween and including an organic material selectively absorbing light in a blue wavelength region, and the red photoelectric device may include electrodes facing each other and an active layer interposed therebetween and including an organic material selectively absorbing light in a red wavelength region.

As described above, the organic photoelectric device selectively absorbing light in a green wavelength region, the organic photoelectric device selectively absorbing light in a red wavelength region, and the organic photoelectric device selectively absorbing light in a blue wavelength region are stacked, and thereby a size of an image sensor may be decreased and a down-sized image sensor may be realized.

The image sensor may be applied to various electronic devices, for example, a mobile phone and/or a digital camera, but is not limited thereto.

Hereinafter, the present disclosure is illustrated in more detail with reference to examples. However, these examples are exemplary, and the present disclosure is not limited thereto.

SYNTHESIS EXAMPLES

Synthesis Example 1

A compound represented by Chemical Formula 1a is synthesized according to Reaction Scheme 1.

[Chemical Formula 1a]

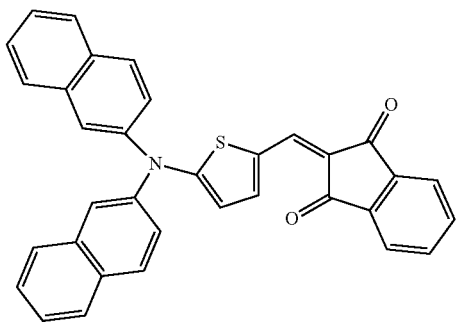

[Reaction Scheme 1]

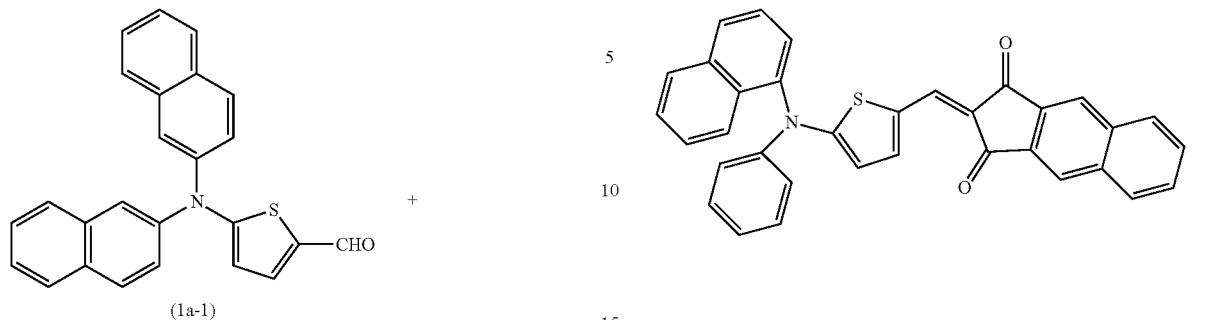

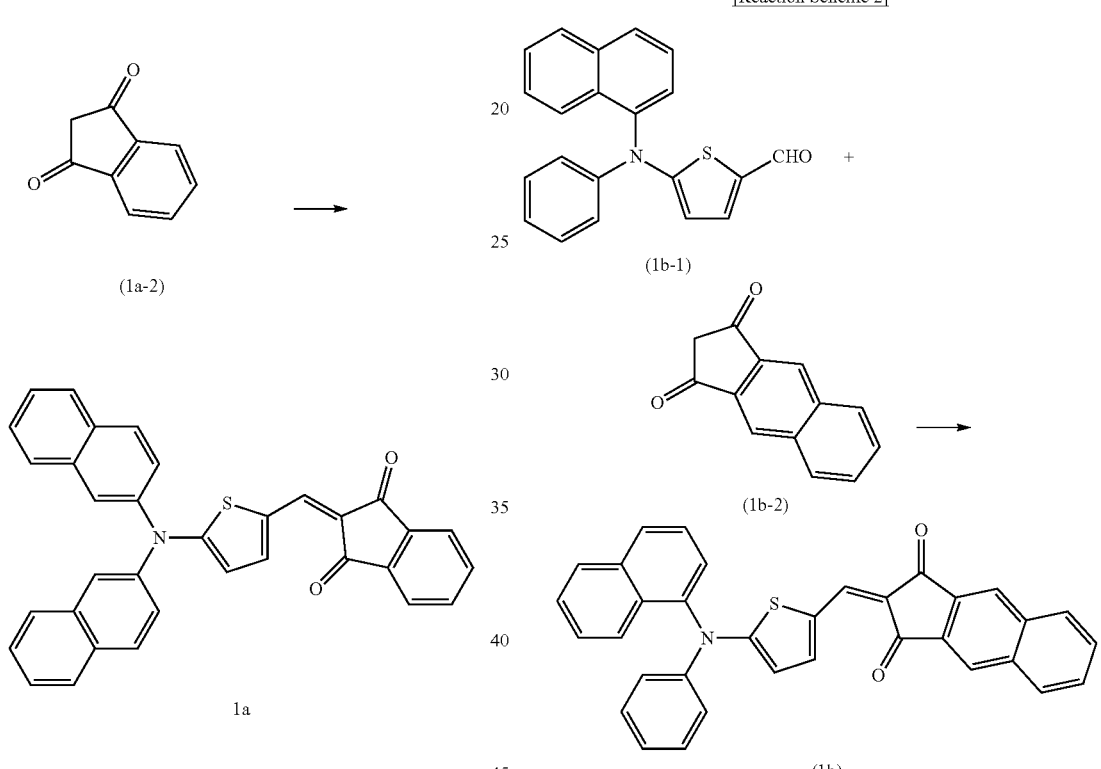

5 g (13.18 mmol) of a compound (1a-1) and 215 g (15.15 mmol) of a compound (1a-2) are put in a three-necked round-bottomed flask, and then dried for 8 hours in a vacuum state and purged with $N_2$ gas. 100 ml of ethanol is added to the reactant, piperidine is added thereto in a dropwise fashion, and then the mixture is refluxed at 75 to 80° C. for 6 hours. The resultant is cooled down to room temperature of 25° C., and water is added thereto. When a powder is formed therein, the powder is filtered, and a filtered solution is purified through column chromatography (developing solvent: dichloromethane/hexane/ethylacetate). Then, dichloromethane and hexane are used to perform recrystallization, obtaining 5.0 g of a compound 1a (with a yield of 75%).

Figure 8:
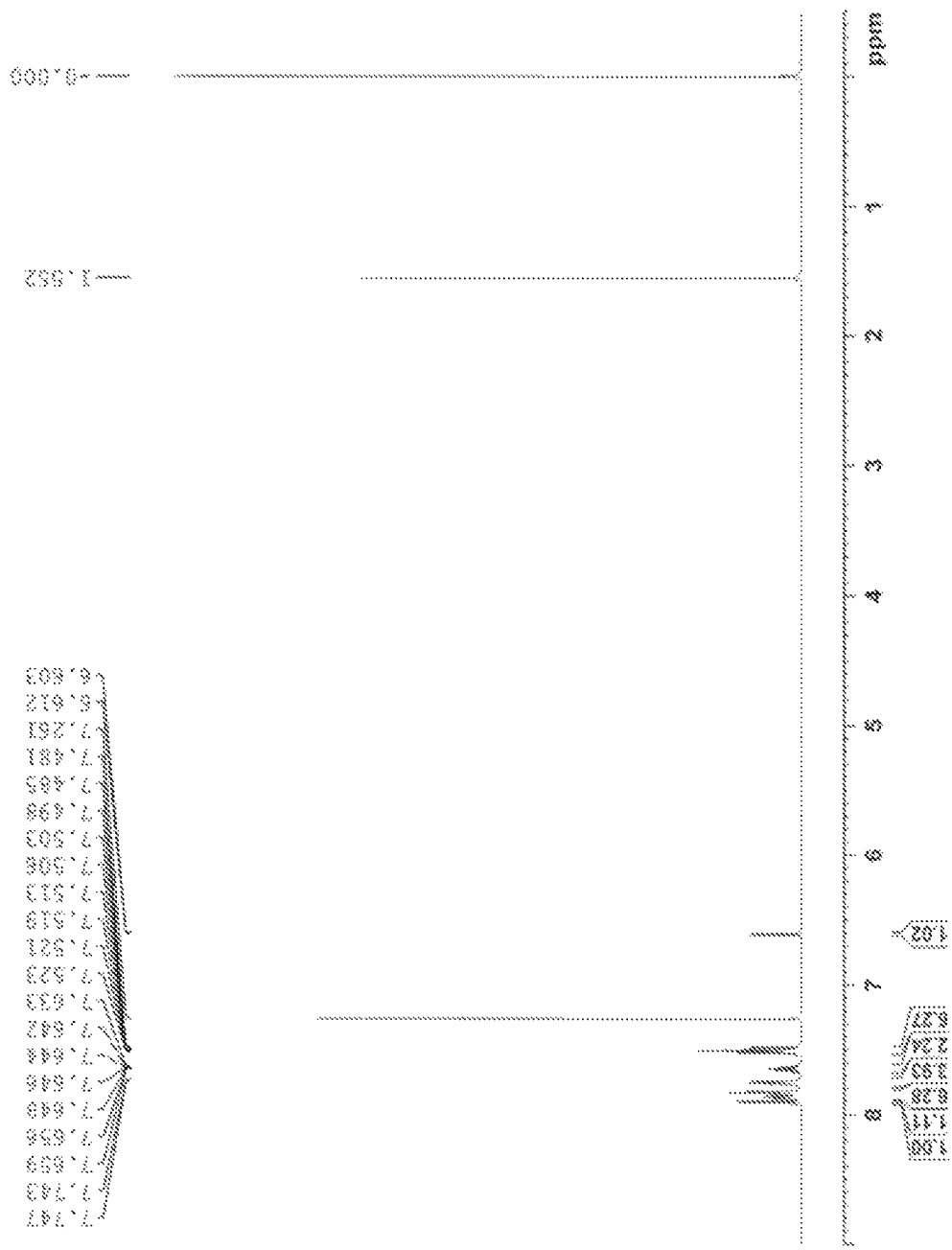
FIG. 8 is a graph showing $^1$H NMR data of the compound according to Synthesis Example 1.

FIG. 8 is a graph showing $^1$H NMR data of the compound represented by Chemical Formula 1a.

Synthesis Example 2

A compound represented by Chemical Formula 1b is synthesized according to Reaction Scheme 2.

5 g (15.18 mmol) of a compound (1b-1) and 3.425 g (17.46 mmol) of a compound (1b-2) are put in a three-necked round-bottomed flask and dried for 8 hours in a vacuum state, and then purged with $N_2$ gas. 100 ml of ethanol and piperidine are added in a dropwise fashion to the reactant, and then the mixture is refluxed at 75 to 80° C. for 6 hours. The resultant is cooled down to room temperature of 25° C., and water is added thereto. When the powder is formed, the power is filtered, and the filtered solution is purified through column chromatography (developing solvent: dichloromethane/hexane/ethylacetate). Then, dichloromethane and hexane are used to perform recrystallization, obtaining 6.2 g of a compound (1b) (with a yield of 80%).

Figure 9:
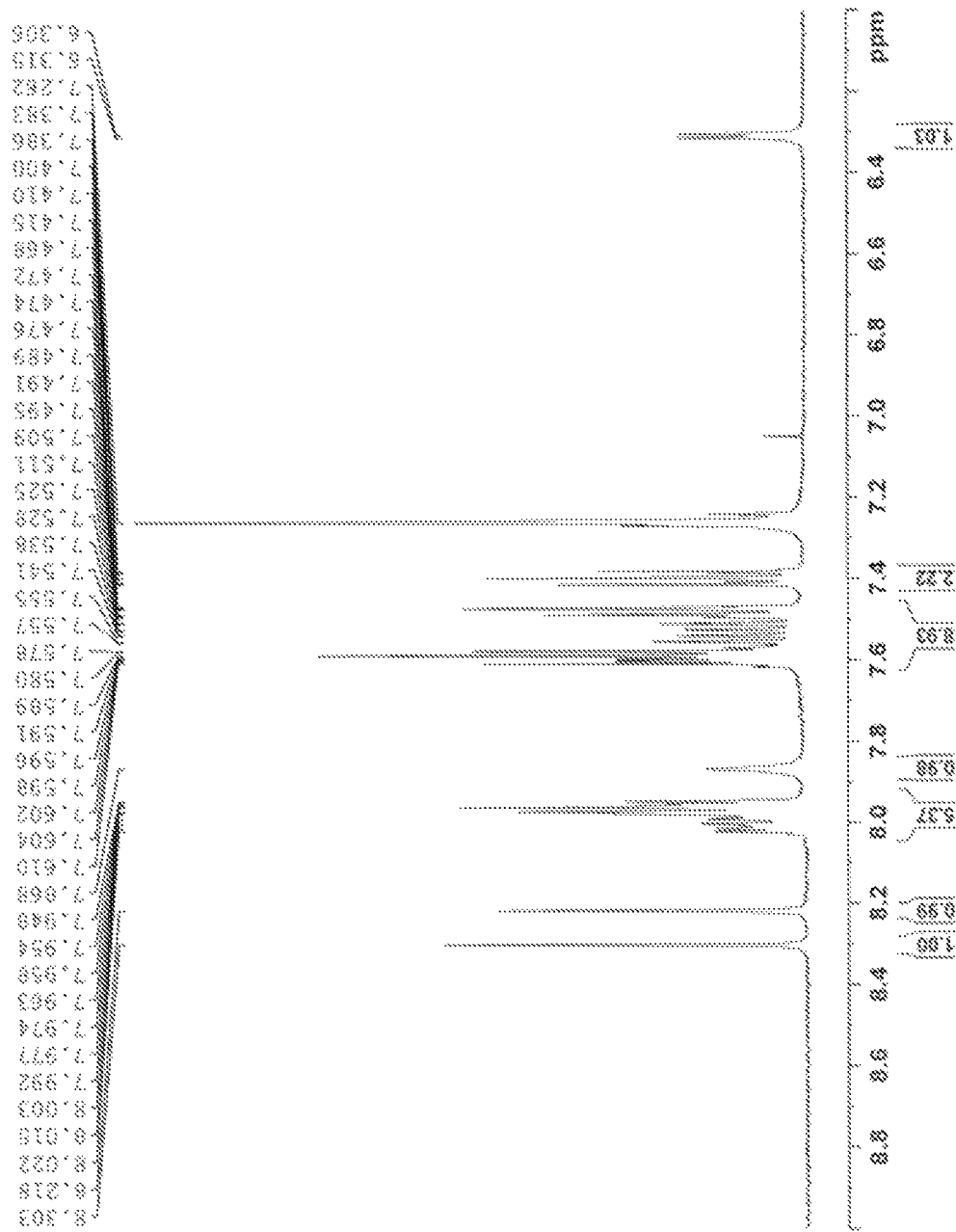
FIG. 9 is a graph showing $^1$H NMR data of the compound according to Synthesis Example 2.

FIG. 9 is a graph showing $^1$H NMR data of the compound represented by Chemical Formula 1b.

Comparative Synthesis Example 1

A compound represented by Chemical Formula 1c is synthesized according to Reaction Scheme 3.

[Chemical Formula 1c]

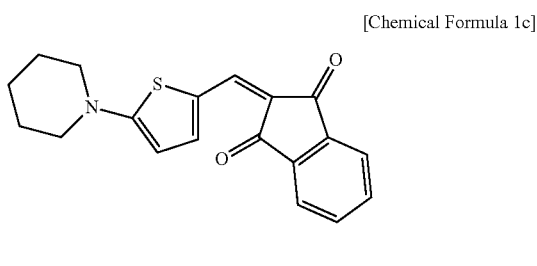 [SMILES: O=C1C(=Cc2ccc(N3CCCCC3)s2)C(=O)c2ccccc21]

[Chemical Formula 1d]

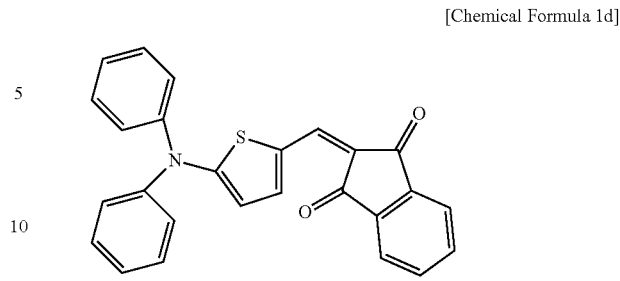

[Reaction Scheme 3]

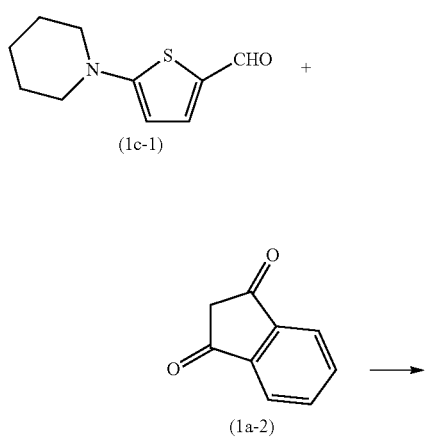

[Reaction Scheme 4]

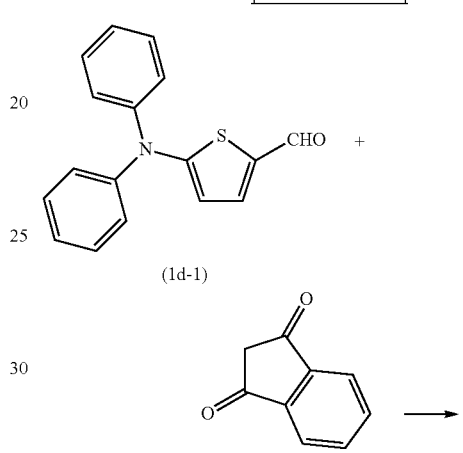

0.1 g (0.512 mmol) of a compound (1c-1) and 0.086 g (0.589 mmol) of a compound (1a-2) are put in a three-necked round-bottomed flask and then dried for 8 hours in a vacuum state and purged with $N_2$ gas. Then, 10 ml of ethanol and piperidine are added to the reactant in a dropwise fashion, and the mixture is refluxed at 75 to 80° C. for 6 hours. The resultant is cooled down to room temperature of 25° C., and water is added thereto. When a powder is formed therein, the powder is filtered, and the filtered solution is purified through column chromatography (developing solvent: dichloromethane/hexane/ethylacetate). Then, dichloromethane and hexane are used to perform recrystallization, obtaining 0.142 g of a compound (1c) (with a yield of 83%).

Figure 10:
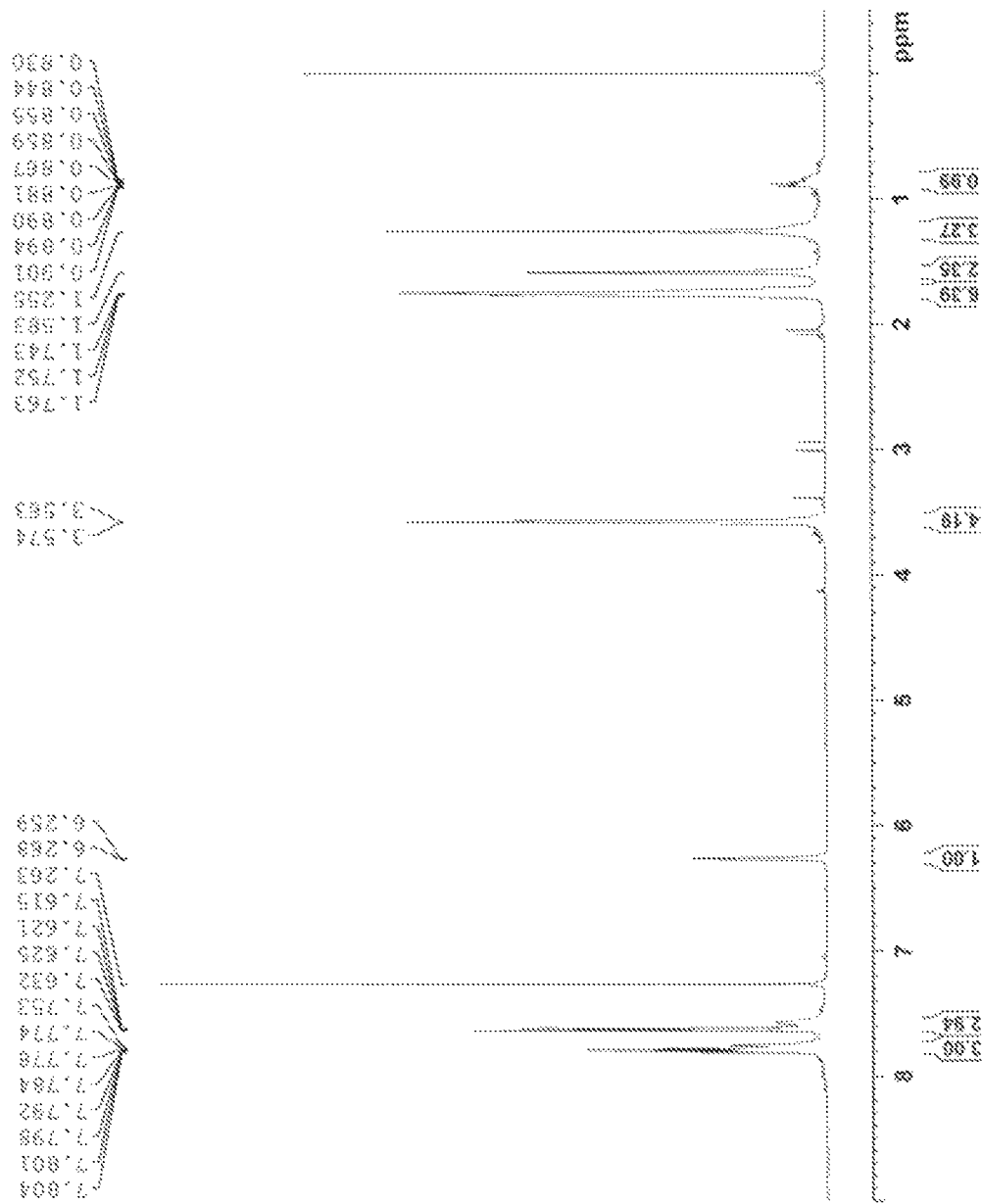
FIG. 10 is a graph showing $^1$H NMR data of the compound according to Comparative Synthesis Example 1.

FIG. 10 is a graph showing $^1$H NMR data of the compound represented by Chemical Formula 1c.

Comparative Synthesis Example 2

A compound represented by Chemical Formula 1d is synthesized according to Reaction Scheme 4.

0.2 g (0.716 mmol) of a compound (1d-1) and 0.12 g (0.823 mmol) of a compound (1a-2) are put in a three-necked round-bottomed flask and then dried for 8 hours in a vacuum state and purged with $N_2$ gas. Then, 15 ml of ethanol and piperidine are added to the reactant in a dropwise fashion, and the mixture is refluxed at 75 to 80° C. for 6 hours. The resultant is cooled down to room temperature of 25° C., and water is added thereto. When a powder is formed, the powder is filtered, and the filtered solution is purified through column chromatography (developing solvent: dichloromethane/hexane/ethylacetate). Then, dichloromethane and hexane are used to perform recrystallization, obtaining 0.16 g of a compound (1d) (with a yield of 5%).

Figure 11:
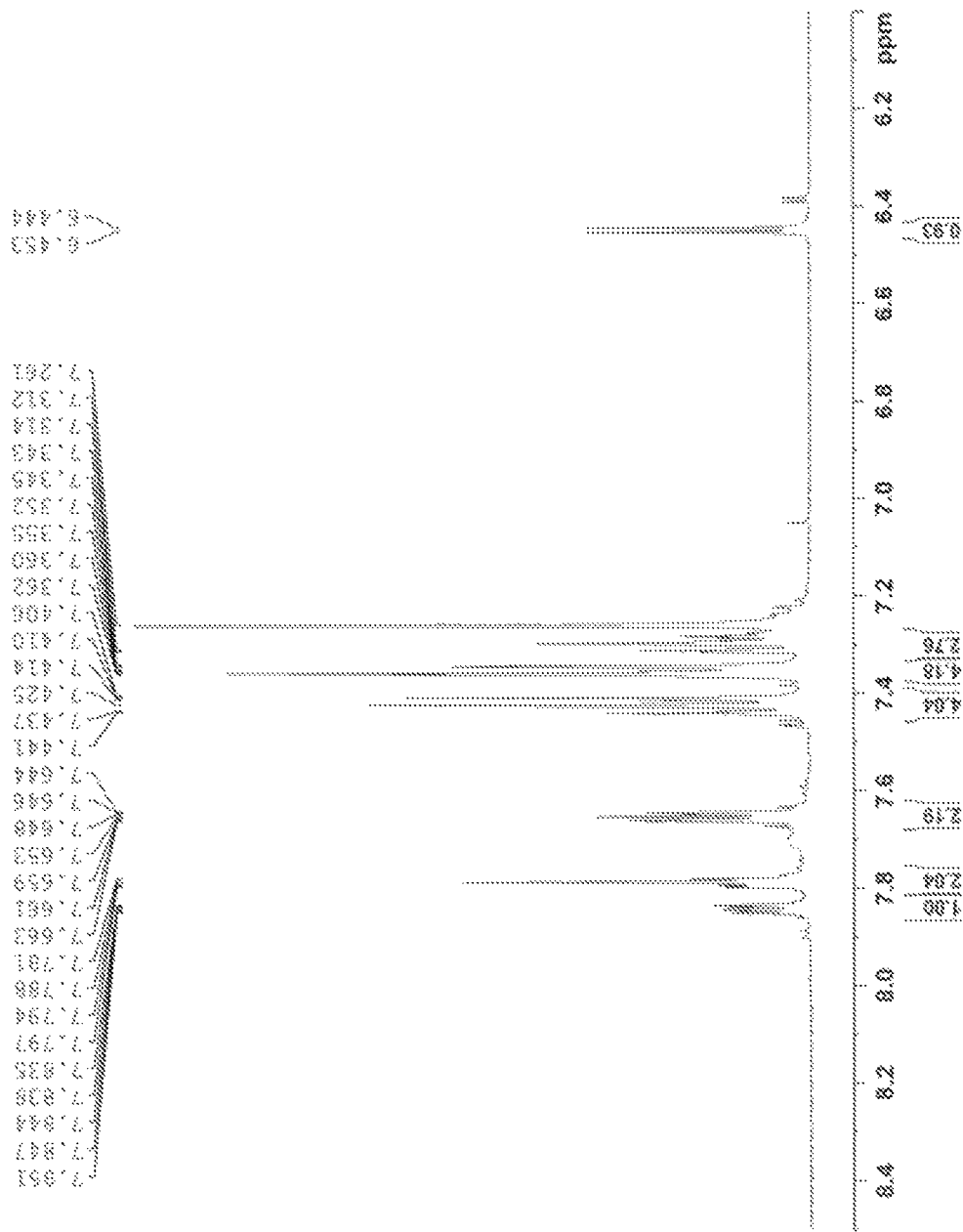
FIG. 11 is a graph showing $^1$H NMR data of the compound according to Comparative Synthesis Example 2.

FIG. 11 is a graph showing $^1$H NMR data of the compound represented by Chemical Formula 1d.

Comparative Synthesis Example 3

A compound (2-((5-(diphenylamino)thiophen-2-yl)methylene)-1H-cyclopenta[b]naphthalene-1,3(2H)-dione) represented by Chemical Formula 1e is prepared.

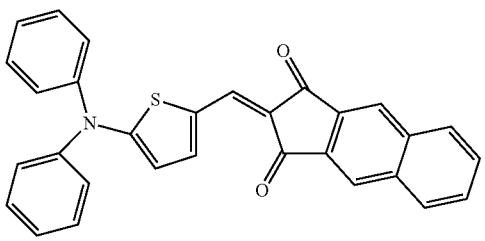

Comparative Synthesis Example 4

A compound (2-((5-(diphenylamino)thiophen-2-yl)methylene)-1H-cyclopenta[b]anthracene-1,3(2H)-dione) represented by Chemical Formula 1 f is prepared.

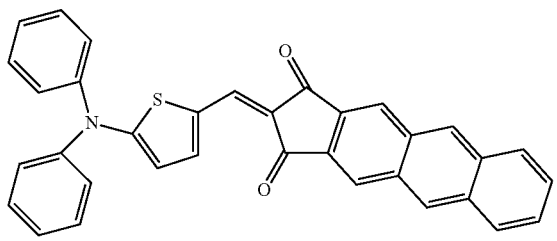

Comparative Synthesis Example 5

A compound (2-((5-((3,5-dimethylphenyl)(naphthalen-1-yl)amino)thiophen-2-yl)methylene)-1H-indene-1,3(2H)-dione) represented by Chemical Formula 1g is prepared.

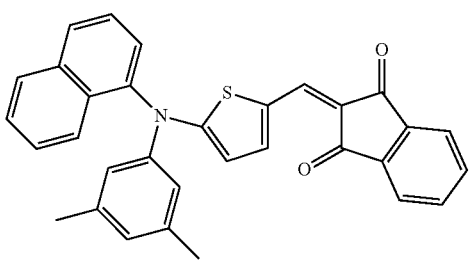

Comparative Synthesis Example 6

A compound (2-((5-(di(naphthalen-1-yl)amino)thiophen-2-yl)methylene)-1H-cyclopenta[b]naphthalene-1,3(2H)-dione) represented by Chemical Formula 1h is prepared.

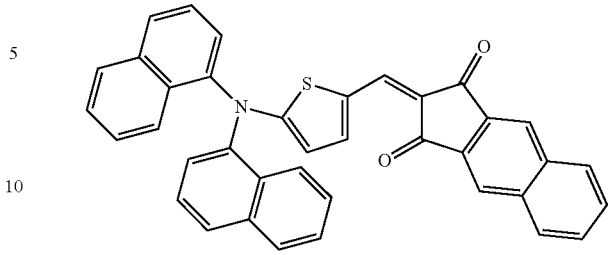

Light Absorption Characteristics of Compounds of Synthesis Examples 1 and 2 and Comparative Synthesis Examples 1 to 6

The compounds according to Synthesis Examples 1 and 2 and Comparative Synthesis Examples 1 to 6 are respectively thermally evaporated at a rate of 0.5-1.0 Å/s under high vacuum (<$10^{-7}$ Torr) to obtain each 70 nm-thick thin film, and ultraviolet (UV)-visible ray (UV-Vis) is radiated into the thin film by using a Cary 5000 UV spectroscope (Varian Inc.) to evaluate its light absorption characteristics. Maximum absorption wavelength of the compounds in a thin film state is measured by using a UV-2450 UV-Visible Spectrophotometer (Shimadzu Co.), and their full width at half maximum (FWHM) is calculated by using a Gaussian simulation. The results of Synthesis Examples 1 and 2 and Comparative Synthesis Examples 2 to 6 are provided in Table 1.

Figure 12:
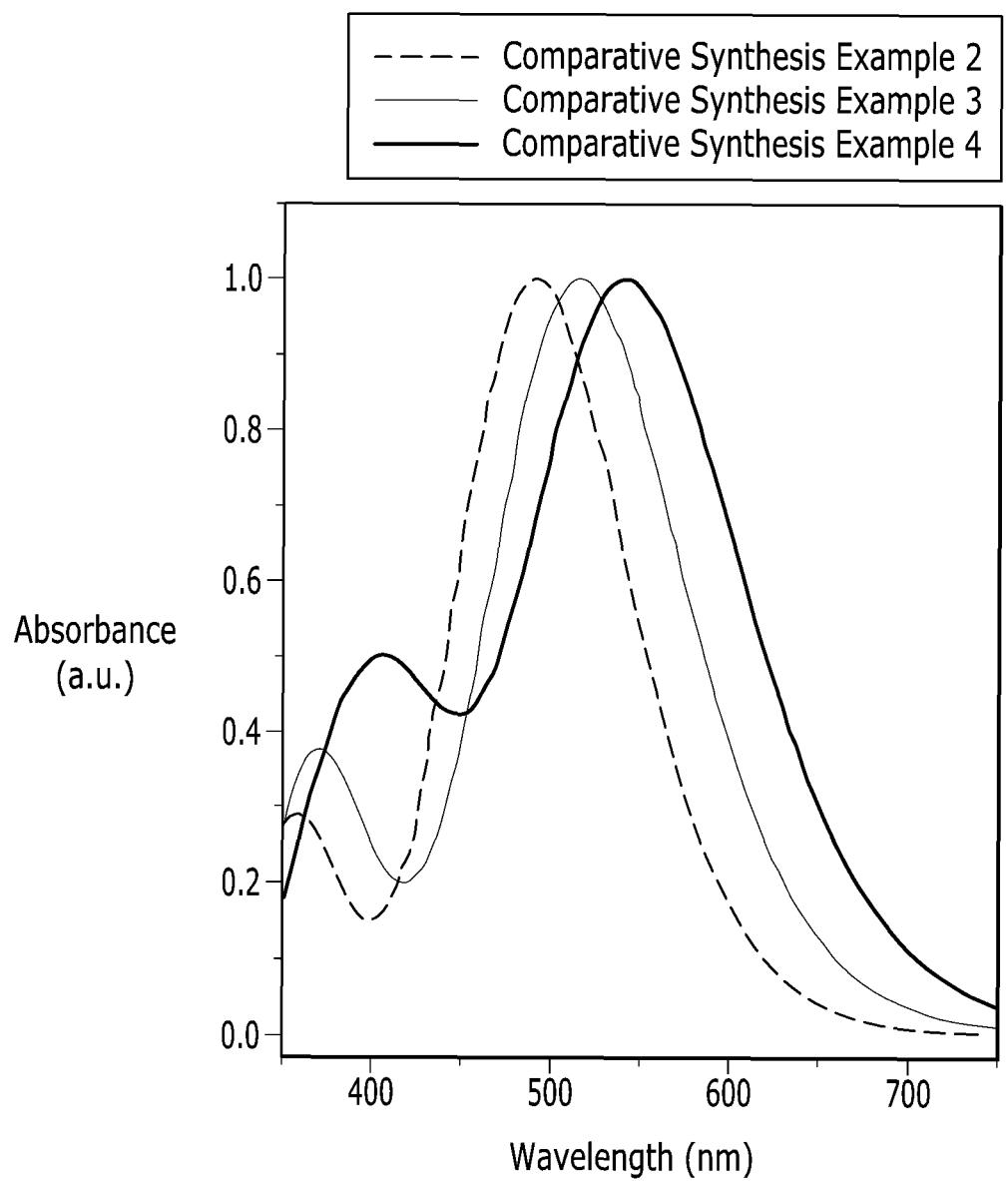
FIG. 12 shows light absorption curves of the compounds according to Comparative Synthesis Examples 2 to 4 in a thin film state.
Figure 13:
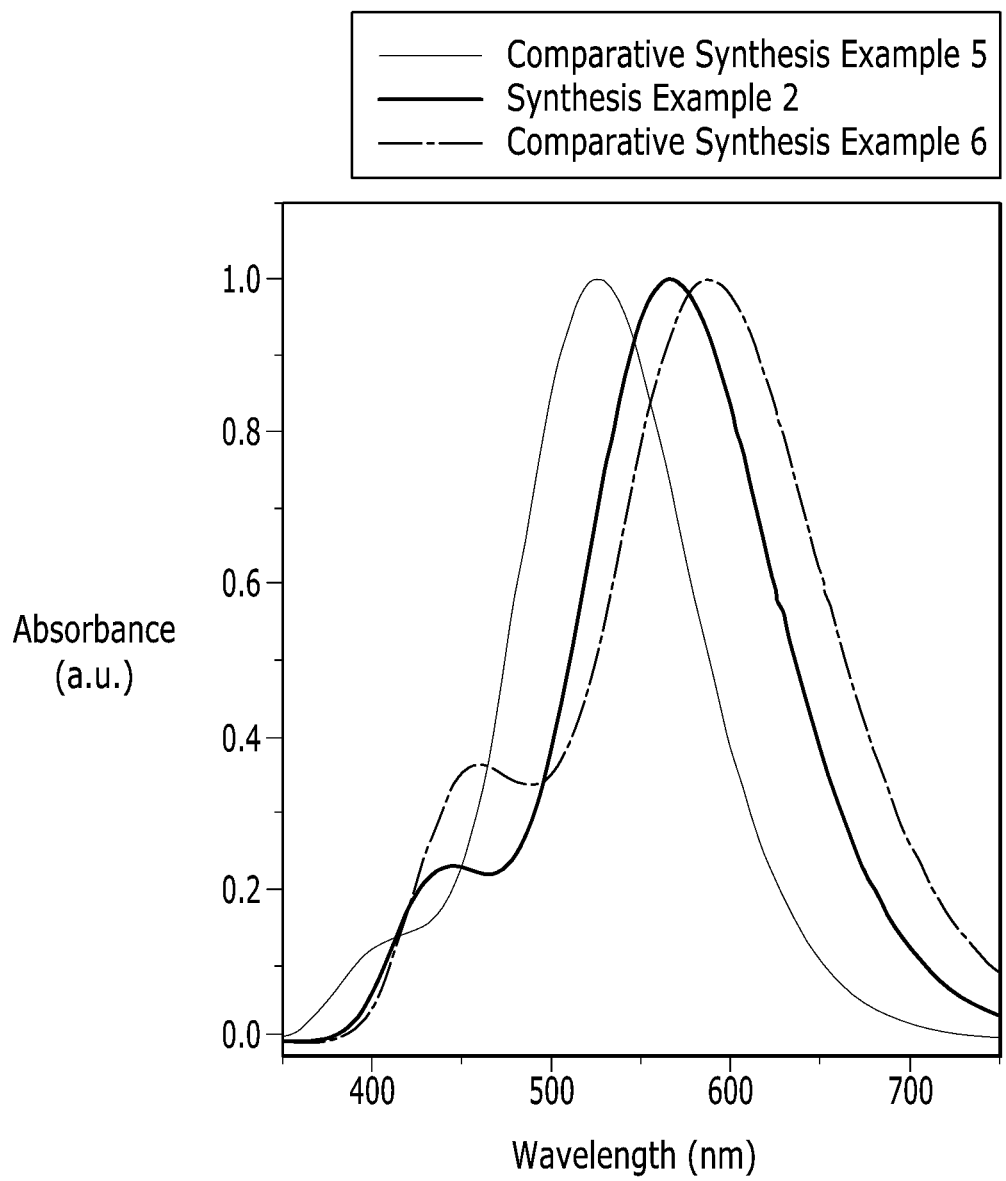
FIG. 13 is a light absorption curves of the compounds according to Synthesis Example 2 and Comparative Synthesis Examples 5 and 6 in a thin film state.

FIG. 12 shows the light absorption curves of the compounds of Comparative Synthesis Examples 2 to 4 in a thin film state, and FIG. 13 shows the light absorption curves of the compounds of Synthesis Example 2 and Comparative Synthesis Examples 5 and 6 in a thin film state in order to facilitate comparison of the maximum absorption wavelengths depending on the number of aromatic rings.

Figure 14:
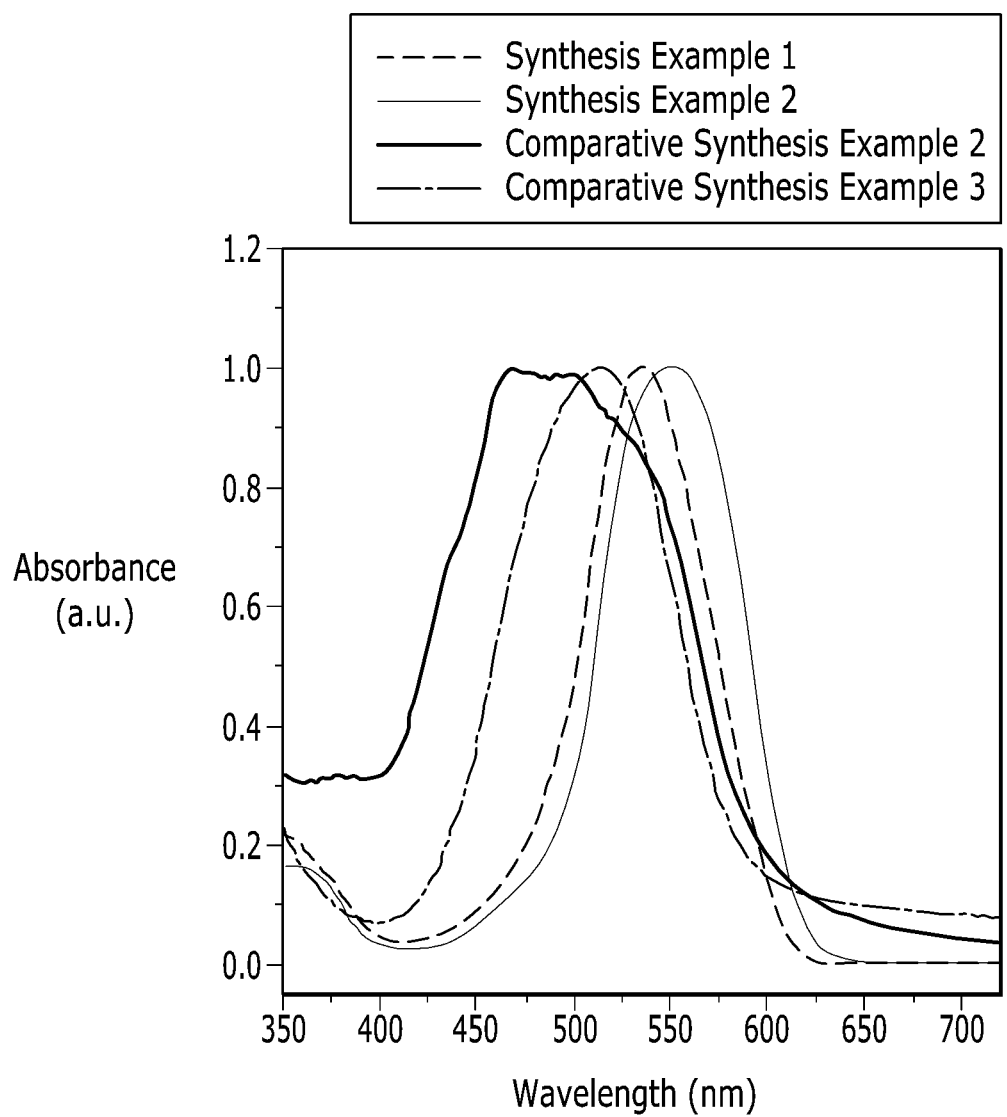
FIG. 14 is a light absorption curves of the compounds according to Synthesis Examples 1 and 2 and Comparative Synthesis Examples 2 and 3 in a thin film state.

In addition, FIG. 14 shows the light absorption curves of the compounds of Synthesis Examples 1 and 2 and Comparative Synthesis Examples 2 and 3 in a thin film state for easy comparison of the light absorption curves depending on the presence of a naphthyl group at a position of $Ar^1$ and $Ar^2$ in Chemical Formula 1.

TABLE 1

| Synthesis Example # (Number of aromatic rings) | Maximum absorption wavelength ($\lambda_{max}$, nm) | Full width at half maximum (FWHM) (nm) |
|---|---|---|
| Synthesis Example 1 (7) | 541 | 99 |
| Synthesis Example 2 (7) | 566 | 94 |
| Comparative Synthesis Example 2 (5) | 469 | 145 |
| Comparative Synthesis Example 3 (6) | 515 | 101 |
| Comparative Synthesis Example 4 (7) | 541 | 150 |
| Comparative Synthesis Example 5 (6) | 525 | 114 |
| Comparative Synthesis Example 6 (8) | 588 | 141 |

Referring to the results of FIGS. 12 to 14 and Table 1, the compounds of Synthesis Examples 1 and 2 in a thin film state respectively have a maximum absorption wavelength ($\lambda_{max}$) at 541 nm and 566 nm and a full width at half maximum (FWHM) of 99 nm and 94 nm, and thus show improved selective absorption of light in a green wavelength region. In addition, their absorption wavelength curves are similar to a Gaussian distribution.

On the contrary, the compounds having 5 or 6 aromatic rings according to Comparative Synthesis Examples 2 and 3 show a maximum absorption wavelength at less than 530 nm, which moves toward a blue wavelength. In addition, the compound having 8 aromatic rings according to Comparative Synthesis Example 6 shows that its maximum absorption wavelength moved to a red wavelength.

In addition, the compounds having no naphthyl group as at least one substituent out of $Ar^1$ and $Ar^2$ in Chemical Formula 1 according to Comparative Synthesis Examples 2 to 4 have too large a full width at half maximum (FWHM), and thus have low selective absorption in a green wavelength region. On the other hand, as for the compounds having a naphthyl group as at least one substituent out of $Ar^1$ and $Ar^2$ in Chemical Formula 1 according to Synthesis Examples 1 and 2, the naphthyl group decreases intermolecular interaction among molecules in a film state, and thus suppresses agglomeration of the molecules and may maintain a narrow full width at half maximum (FWHM) in the light absorption curves. Accordingly, selective absorption in a green wavelength region is increased.

Thermal Characteristics of Compounds of Synthesis Examples 1 and 2 and Comparative Synthesis Example 2

The melting points and the thermal decomposition temperatures of the compounds according to Synthesis Examples 1 and 2 and Comparative Synthesis Example 2 are measured and provided in the following Table 2. The thermal decomposition temperature ($T_d$) is a temperature at which a compound starts to be decomposed and thus, does not maintain its intrinsic molecular structure but is transformed. In general, atoms in a molecule consisting of a compound are volatilized and lost into the air or vacuum at greater than or equal to a thermal decomposition temperature, and thus, the thermal decomposition temperature may be regarded as a temperature at which initial weight of the compound starts to be decreased by 5% by heat. Herein, a thermal gravimetric analysis (TGA) method is used to measure the thermal decomposition temperature.

TABLE 2

| | Melting point ($T_m$) | Thermal decomposition temperature ($T_d$) |
|---|---|---|
| Synthesis Example 1 | 242° C. | 280° C. |
| Synthesis Example 2 | 304° C. | 269° C. |
| Comparative Synthesis Example 2 | 240° C. | 266° C. |

Referring to the results of Table 2, the compounds of Synthesis Examples 1 and 2 show a high melting point and a high thermal decomposition temperature, and thus have improved thermal stability and may be appropriate for a deposition process.

Manufacture of Organic Photoelectric Device

Example 1

An about 100 nm-thick anode is formed by sputtering ITO on a glass substrate, and a 10 nm-thick molybdenum oxide ($MoO_x$, $0<x\leq3$) thin film is laminated as a charge auxiliary layer thereon. Subsequently, an 85 nm-thick active layer is formed by codepositing the compound of Chemical Formula 1a according to Synthesis Example 1 (a p-type semiconductor compound) and C60 (an n-type semiconductor compound) in a thickness ratio of 1:1 on the molybdenum oxide ($MoO_x$) thin film. On the active layer, an 80 nm-thick cathode is formed by sputtering aluminum (Al), manufacturing an organic photoelectric device.

Example 2

An organic photoelectric device is manufactured according to the same method as Example 1, except for using the compound of Chemical Formula 1b according to Synthesis Example 2 (a p-type semiconductor compound) instead of the compound (a p-type semiconductor compound) of Synthesis Example 1.

Comparative Examples 1 to 6

Each organic photoelectric device is manufactured according to the same method as Example 1, except for respectively using the compounds of Chemical Formulae 1c to 1h of Comparative Synthesis Examples 1 to 6 (a p-type semiconductor compound) instead of the compound (a p-type semiconductor compound) of Synthesis Example 1.

Example 3

An about 100 nm-thick anode is formed by sputtering ITO on a glass substrate, and a 20 nm-thick molybdenum oxide ($MoO_x$, $0<x\leq3$) thin film is laminated as a charge auxiliary layer thereon. Subsequently, an 70 nm-thick active layer is formed by codepositing the compound of Chemical Formula 1b according to Synthesis Example 2 (a p-type semiconductor compound) and an n-type semiconductor compound of Chemical Formula 2a in a thickness ratio of 1:1 on the molybdenum oxide ($MoO_x$, $0<x\leq3$) thin film. On the active layer, an 80 nm-thick cathode is formed by sputtering aluminum (Al), manufacturing an organic photoelectric device.

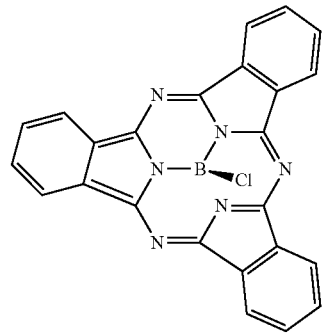

[Chemical Formula 2a]

Example 4

An organic photoelectric device is manufactured according to the same method as Example 3, except for using a n-type semiconductor compound of Chemical Formula 2b instead of the n-type semiconductor compound of Chemical Formula 2a.

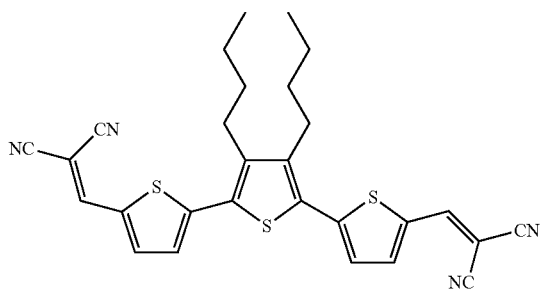

Example 5

An organic photoelectric device is manufactured according to the same method as Example 3, except for using a n-type semiconductor compound of Chemical Formula 2c instead of the n-type semiconductor compound of Chemical Formula 2a.

[Chemical Formula 2c]

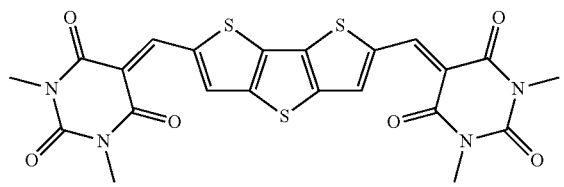

External Quantum Efficiency (EQE)

External quantum efficiency (EQE) of the organic photoelectric devices according to Examples 1 to 5 and Comparative Example 3 depending on a wavelength and voltage is evaluated.

The external quantum efficiency is measured by using an IPCE measurement system (McScience Co., Ltd. Korea). First, the IPCE measurement system is calibrated by using a Si photodiode (Hamamatsu Photonics K.K., Japan), and then the organic photoelectric devices of Examples 1 and 2 are respectively mounted thereon, and their external quantum efficiency in a wavelength region of about 300 to 700 nm is determined.

Figure 15:
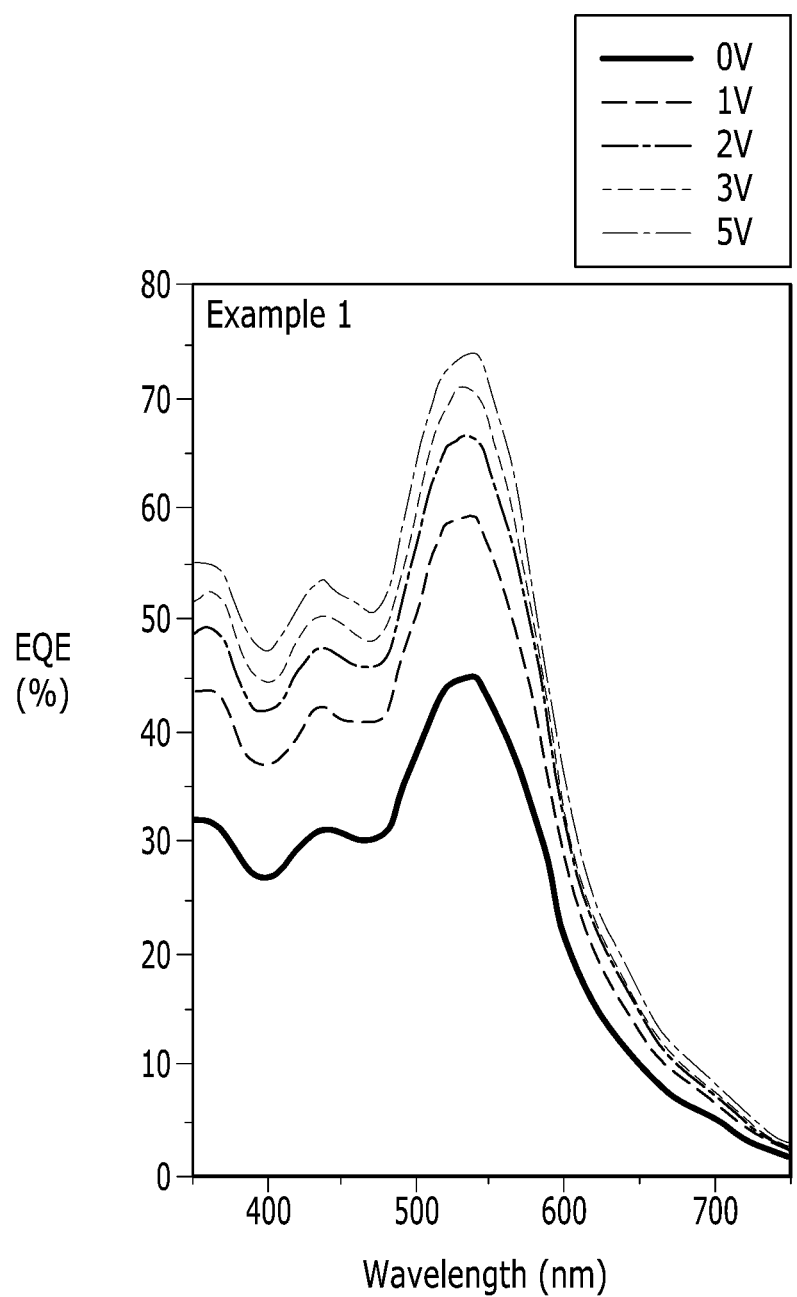
FIG. 15 shows external quantum efficiency (EQE) depending on a wavelength and a voltage of the organic photoelectric device according to Example 1.
Figure 16:
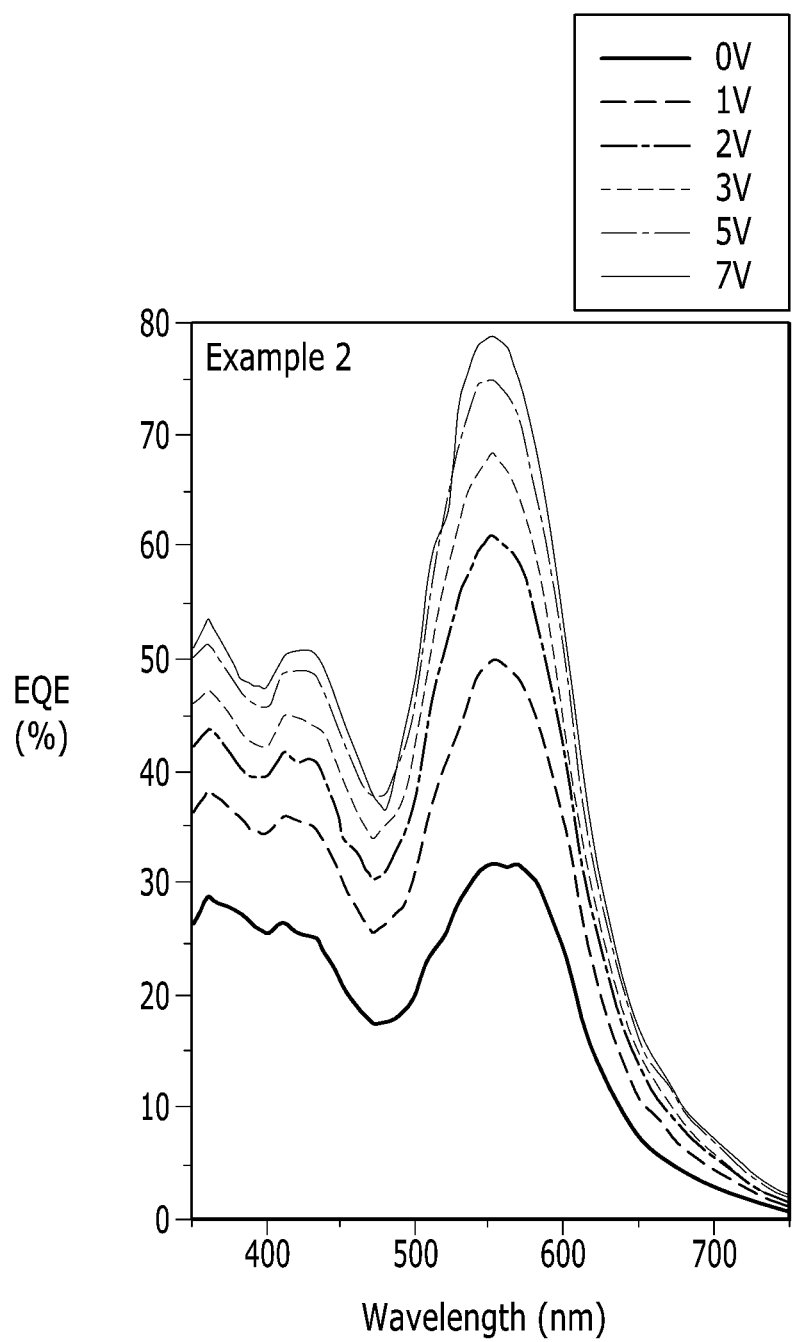
FIG. 16 shows external quantum efficiency (EQE) depending on a wavelength and a voltage of the organic photoelectric device according to Example 2.
Figure 17:
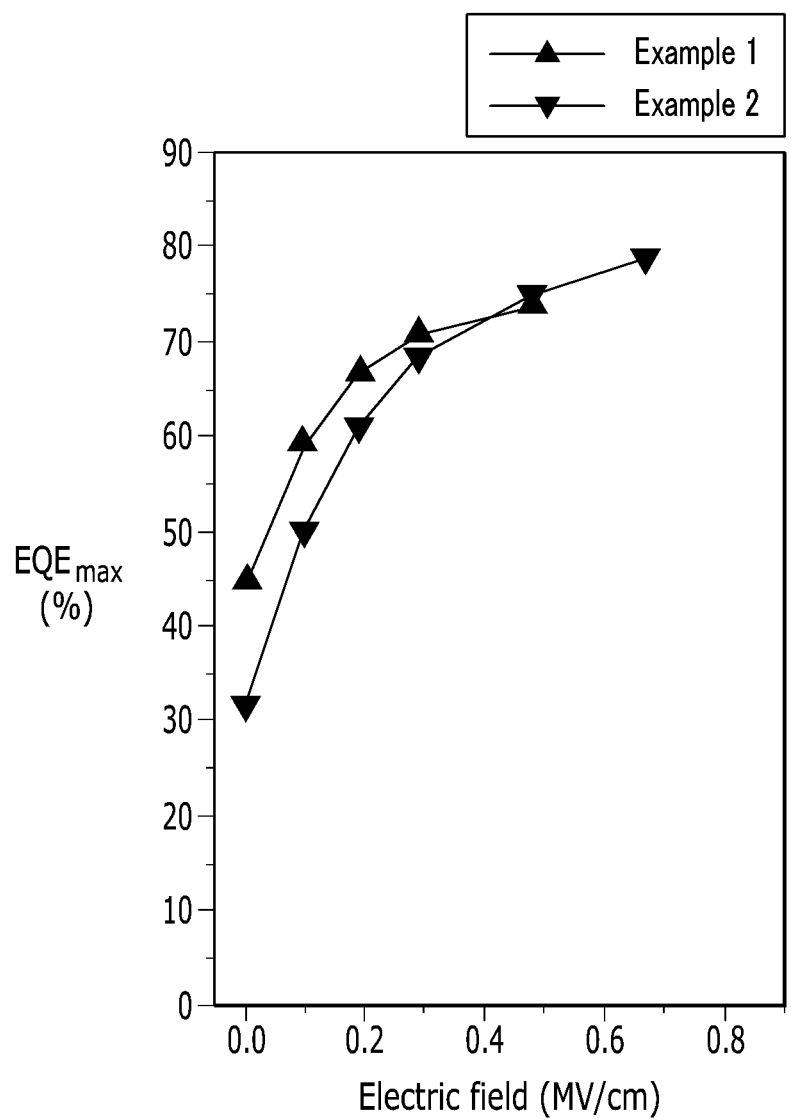
FIG. 17 shows external quantum efficiency ($EQE_{max}$) depending on an electric field of the organic photoelectric devices according to Examples 1 and 2.
Figure 18:
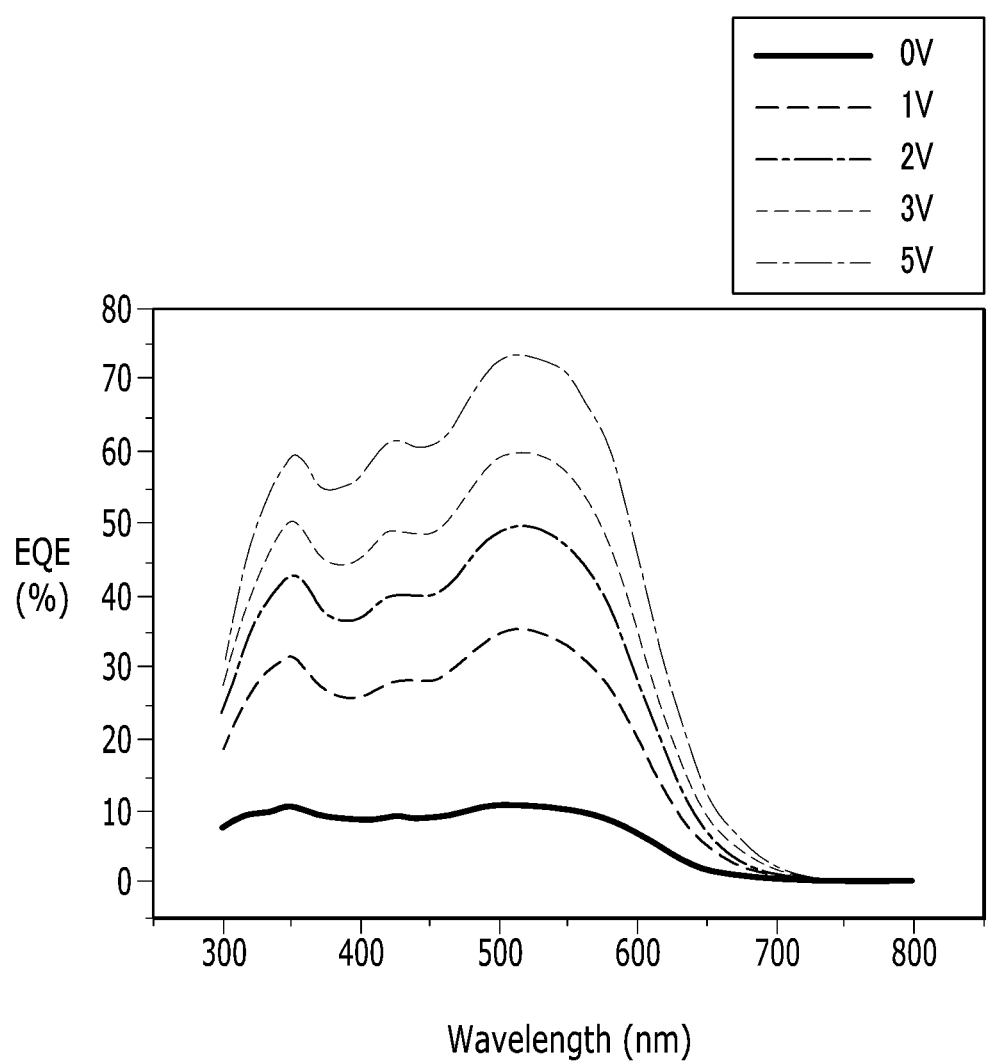
FIG. 18 shows external quantum efficiency (EQE) depending on a wavelength and a voltage of the organic photoelectric device according to Comparative Example 3.

FIGS. 15 and 16 show external quantum efficiency (EQE) of the organic photoelectric devices according to Examples 1 and 2 depending on a wavelength and a voltage, respectively. FIG. 17 shows external quantum efficiency ($EQE_{max}$) of the organic photoelectric devices according to Examples 1 and 2 depending on an electric field. FIG. 18 shows external quantum efficiency (EQE) of the organic photoelectric device according to Comparative Example 3 depending on a wavelength and a voltage.

Referring to FIGS. 15 and 16, the organic photoelectric devices according to Example 1 and 2 show sufficient external quantum efficiency (EQE) in a green wavelength region of about 530 nm to 570 nm. Referring to FIG. 15, the organic photoelectric device of Example 1 shows external quantum efficiency (EQE) of 71 at 3 V, and referring to FIG. 16, Example 2 shows improved external quantum efficiency (EQE) of 69% at 3 V. Referring to FIG. 18, the organic photoelectric device of Comparative Example 3 shows insufficient wavelength selectivity and external quantum efficiency.

Figure 19:
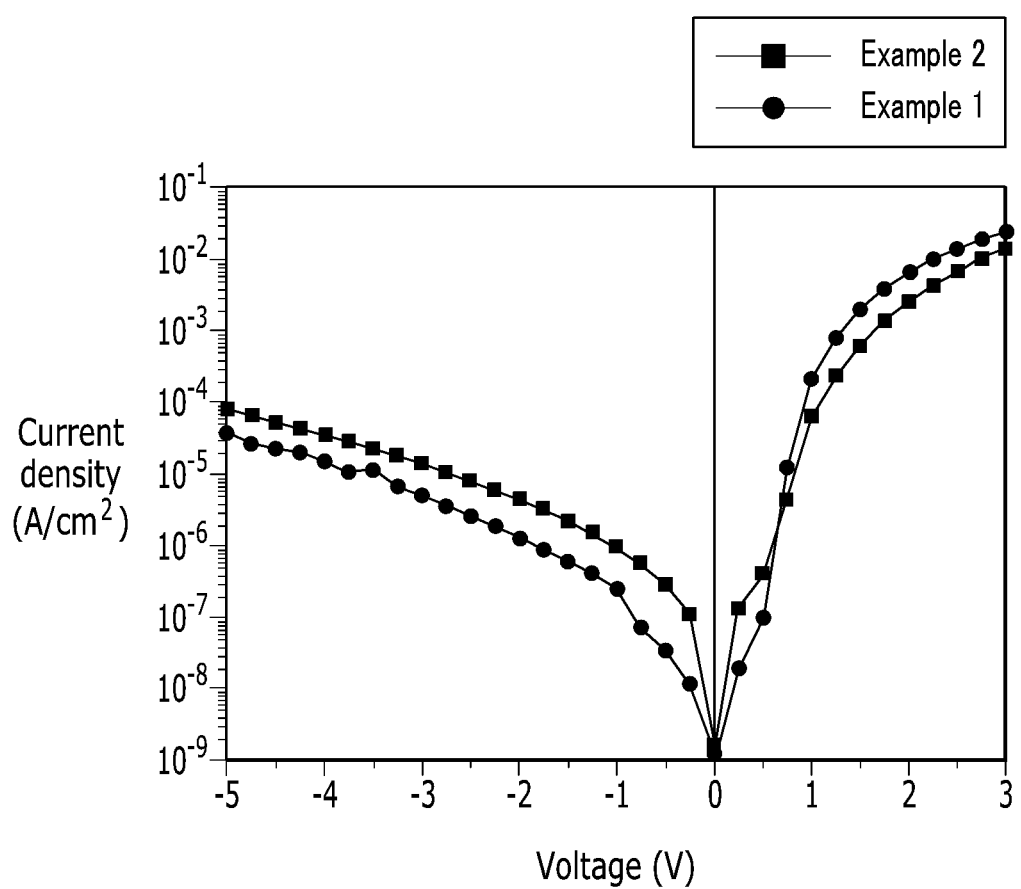
FIG. 19 shows current density depending on a voltage of the organic photoelectric devices according to Examples 1 and 2.

FIG. 19 shows current density of the organic photoelectric devices according to Examples 1 and 2 depending on a voltage. Referring to FIG. 19, the organic photoelectric devices according to Examples 1 and 2 show that a dark current decreases, which shows their stable characteristics.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A compound for an organic photoelectric device represented by Chemical Formula 1:

[Chemical Formula 1]

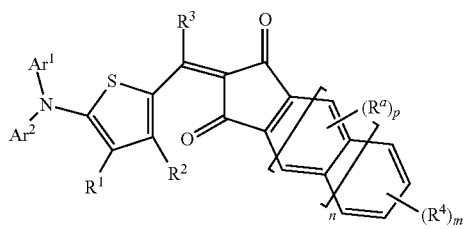

wherein, in Chemical Formula 1,
each of $Ar^1$ and $Ar^2$ are independently one of a phenyl group and a naphthyl group, provided at least one of $Ar^1$ and $Ar^2$ is a naphthyl group,
each of $R^1$ to $R^4$ are independently one of hydrogen, a $C_1$ to $C_6$ alkyl group, a $C_1$ to $C_6$ haloalkyl group, a halogen, and CN,
$R^a$ is one of hydrogen, a $C_1$ to $C_6$ alkyl group, a $C_1$ to $C_6$ haloalkyl group, a halogen, and CN,
p is an integer of 1 or 2,
n is 0 or 1,
m is an integer ranging from 1 to 4, and
the compound has 7 aromatic rings.

2. The compound of claim 1, wherein the compound is represented by Chemical Formula 2:

[Chemical Formula 2]

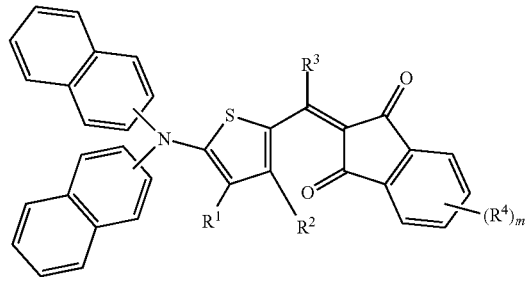

wherein, in Chemical Formula 2,
each of $R^1$ to $R^4$ are independently one of hydrogen, a $C_1$ to $C_6$ alkyl group, a $C_1$ to $C_6$ haloalkyl group, a halogen, and CN, and
m is an integer ranging from 1 to 4.

3. The compound of claim 1, wherein the compound is represented by Chemical Formula 3:

[Chemical Formula 3]

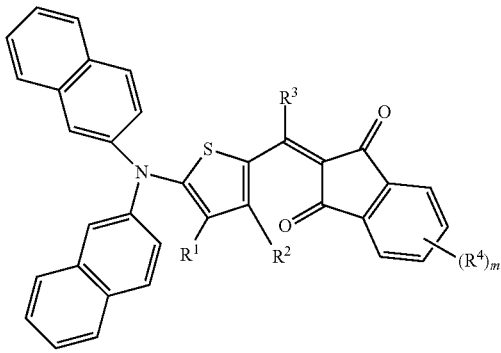

wherein, in Chemical Formula 3,
each of $R^1$ to $R^4$ are independently one of hydrogen, a $C_1$ to $C_6$ alkyl group, a $C_1$ to $C_6$ haloalkyl group, a halogen, and CN, and
m is an integer ranging from 1 to 4.

4. The compound of claim 1, wherein the compound is represented by Chemical Formula 4:

[Chemical Formula 4]

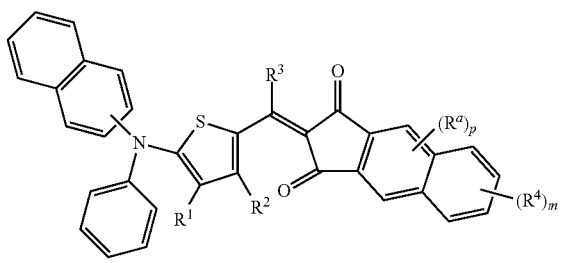

wherein, in Chemical Formula 4,
each of $R^1$ to $R^4$ are independently one of hydrogen, a $C_1$ to $C_6$ alkyl group, a $C_1$ to $C_6$ haloalkyl group, a halogen, and CN,
$R^a$ is independently one of hydrogen, a $C_1$ to $C_6$ alkyl group, a $C_1$ to $C_6$ haloalkyl group, a halogen, and CN,
p is an integer of 1 or 2, and
m is an integer ranging from 1 to 4.

5. The compound of claim 1, wherein the compound is represented by Chemical Formula 5:

[Chemical Formula 5]

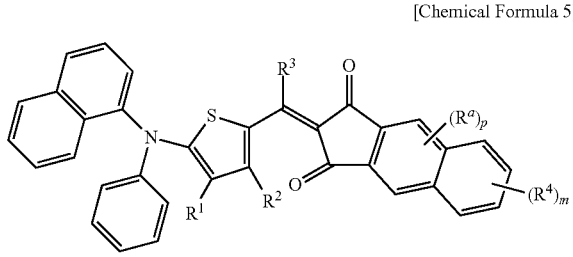

wherein, in Chemical Formula 3,
each of $R^1$ to $R^4$ are independently one of hydrogen, a $C_1$ to $C_6$ alkyl group, a $C_1$ to $C_6$ haloalkyl group, a halogen, and CN,
$R^a$ is independently one of hydrogen, a $C_1$ to $C_6$ alkyl group, a $C_1$ to $C_6$ haloalkyl group, a halogen, and CN,
p is an integer of 1 or 2, and
m is an integer ranging from 1 to 4.

6. The compound of claim 1, wherein the compound has a maximum absorption wavelength ($\lambda_{max}$) of about 530 nm to about 570 nm in a thin film state.

7. The compound of claim 1, wherein the compound shows a light absorption curve having a full width at half maximum (FWHM) of about 50 nm to about 100 nm in a thin film state.

8. The compound of claim 1, wherein the compound is a p-type semiconductor compound.

9. A compound for an organic photoelectric device represented by Chemical Formula 1:

[Chemical Formula 1]

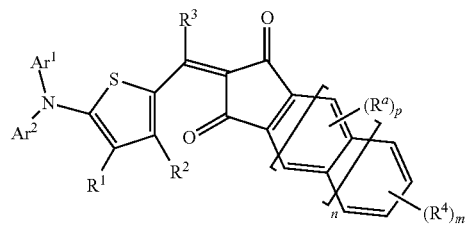

wherein, in Chemical Formula 1,
each of $Ar^1$ and $Ar^2$ are independently one of a phenyl group and a naphthyl group, provided at least one of $Ar^1$ and $Ar^2$ is a naphthyl group,
each of $R^1$ to $R^4$ are independently one of hydrogen, a $C_1$ to $C_6$ alkyl group, a $C_1$ to $C_6$ haloalkyl group, a halogen, and CN,
$R^a$ is one of hydrogen, a $C_1$ to $C_6$ alkyl group, a $C_1$ to $C_6$ haloalkyl group, a halogen, and CN,
p is an integer of 1 or 2,
n is 0 or 1, and
m is an integer ranging from 1 to 4,
the compound having a maximum absorption wavelength ($\lambda_{max}$) of about 530 nm to about 570 nm in a thin film state, and
the compound showing a light absorption curve having a full width at half maximum (FWHM) of about 50 nm to about 100 nm in a thin film state.

10. An organic photoelectric device comprising
a first electrode and a second electrode facing each other, and
an active layer between the first electrode and the second electrode, the active layer including the compound of claim 1.

11. The organic photoelectric device of claim 10, wherein the active layer further comprises an n-type semiconductor compound.

12. The organic photoelectric device of claim 11, wherein the n-type semiconductor compound is one of sub-phthalocyanine, fullerene or a fullerene derivative, thiophene or a thiophene derivative, and a combination thereof.

13. The organic photoelectric device of claim 11, wherein the active layer comprises an intrinsic layer including the compound represented by Chemical Formula 1.

14. The organic photoelectric device of claim 13, wherein the active layer further comprises at least one of a p-type layer on one side of the intrinsic layer and an n-type layer on the other side of the intrinsic layer.

15. The organic photoelectric device of claim 11, wherein the active layer further comprises a second p-type semiconductor compound configured to selectively absorb green light.

16. The organic photoelectric device of claim 15, wherein the second p-type semiconductor compound is represented by Chemical Formula 9:

[Chemical Formula 9]

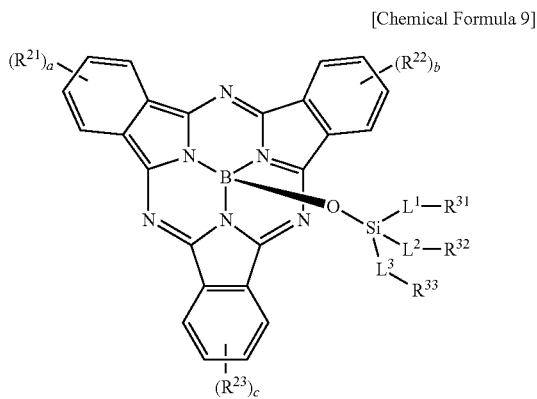

wherein, in Chemical Formula 9,
each of $R^{21}$ to $R^{23}$ are independently one of hydrogen, a substituted or unsubstituted $C_1$ to $C_{30}$ aliphatic hydrocarbon group, a substituted or unsubstituted $C_6$ to $C_{30}$ aromatic hydrocarbon group, a substituted or unsubstituted $C_1$ to $C_{30}$ aliphatic heterocyclic group, a substituted or unsubstituted $C_2$ to $C_{30}$ aromatic heterocyclic group, a substituted or unsubstituted $C_1$ to $C_{30}$ alkoxy group, a substituted or unsubstituted $C_6$ to $C_{30}$ aryloxy group, a thiol group, a substituted or unsubstituted $C_1$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group, and a combination thereof,
$R^{21}$ to $R^{23}$ are independently present or are fused to each other to provide a ring,
each of $L^1$ to $L^3$ are independently one of a single bond, a substituted or unsubstituted $C_1$ to $C_{30}$ alkylene group, a substituted or unsubstituted $C_6$ to $C_{30}$ arylene group, a divalent substituted or unsubstituted $C_3$ to $C_{30}$ heterocyclic group, and a combination thereof, and
each of $R^{31}$ to $R^{33}$ are independently one of a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group, a substituted or unsubstituted silyl group, and a combination thereof.

17. An image sensor comprising the organic photoelectric device of claim 10.

18. The image sensor of claim 17, further comprising:
a semiconductor substrate integrated with a plurality of first photo-sensing devices configured to sense light in a blue wavelength region and a plurality of second photo-sensing devices configured to sense light in a red wavelength region,
wherein the organic photoelectric device is on the semiconductor substrate and selectively absorbs light in a green wavelength region.

19. The image sensor of claim 18, further comprising:
a color filter layer between the semiconductor substrate and the organic photoelectric device, the color filter layer including a blue filter configured to selectively absorb light in a blue wavelength region and a red filter configured to selectively absorb light in a red wavelength region.

20. The image sensor of claim 17, further comprising:
a semiconductor substrate integrated with at least one photo-sensing device, wherein the organic photoelectric device is on the semiconductor substrate.

21. The image sensor of claim 20, wherein
the at least one photo-sensing device includes a first photo-sensing device configured to sense light in a blue wavelength region and a second photo-sensing device configured to sense light in a red wavelength region, and
the first photo-sensing device and the second photo-sensing device are stacked in a vertical direction on the semiconductor substrate.

22. The image sensor of claim 17, wherein
the organic photoelectric device is a green photoelectric device, and
the image sensor comprises the green photoelectric device, a blue photoelectric device configured to selectively absorb light in a blue wavelength region, and a red photoelectric device configured to selectively absorb light in a red wavelength region that are stacked.

23. The image sensor of claim 17, wherein
the compound included in the active layer is a p-type semiconductor compound,
the active layer further includes an n-type semiconductor compound, and
the p-type semiconductor compound and the n-type semiconductor compound form a pn junction.

24. An electronic device comprising the image sensor of claim 17.

* * * * *